US009588195B2

(12) United States Patent
Fichtinger et al.

(10) Patent No.: US 9,588,195 B2
(45) Date of Patent: *Mar. 7, 2017

(54) APPARATUS FOR INSERTION OF A MEDICAL DEVICE DURING A MEDICAL IMAGING PROCESS

(71) Applicant: The Johns Hopkins University, Baltimore, MD (US)

(72) Inventors: Gabor Fichtinger, Kingston (CA); Ergin Atalar, Bilkent Ankara (TR); Louis L. Whitcomb, Baltimore, MD (US); Robert C. Susil, Baltimore, MD (US); Axel Krieger, San Antonio, TX (US); Attila Tanacs, Zakanyszek (HU)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/200,910

(22) Filed: Mar. 7, 2014

(65) Prior Publication Data

US 2014/0187913 A1    Jul. 3, 2014

Related U.S. Application Data

(60) Continuation of application No. 13/546,782, filed on Jul. 11, 2012, now Pat. No. 8,706,186, which is a
(Continued)

(51) Int. Cl.
*A61B 5/05* (2006.01)
*G01R 33/28* (2006.01)
(Continued)

(52) U.S. Cl.
CPC ............ *G01R 33/287* (2013.01); *A61B 5/055* (2013.01); *A61B 5/06* (2013.01); *A61B 6/12* (2013.01); *A61B 8/0833* (2013.01); *A61B 8/0841* (2013.01); *A61B 10/0241* (2013.01); *A61B 17/3403* (2013.01); *A61B 17/3478* (2013.01); *A61B 34/20* (2016.02); *A61B 8/12* (2013.01);
(Continued)

(58) Field of Classification Search
CPC .... A61F 2/95; A61F 2/966; A61F 2/06; A61F 2/91
USPC ........ 600/407, 437, 439, 427, 462, 464, 459
See application file for complete search history.

(56) References Cited

U.S. PATENT DOCUMENTS 5,471,988 A    12/1995  Fujio et al.
5,715,825 A *  2/1998  Crowley ................ A61B 5/416
                                                              600/462
(Continued)

OTHER PUBLICATIONS

S. Lee, G. Fichtinger, and G. Chirikjian, "Numerical algorithms for spatial registration of line fiducials from cross-sectional images," Med. Phys. 29(8), Aug. 2002, pp. 1881-1891.

*Primary Examiner* — Joel Lamprecht
(74) *Attorney, Agent, or Firm* — Mintz Levin Cohn Ferris Glovsky and Popeo, P.C.; Peter F. Corless; Richard B. Emmons

(57) ABSTRACT

The end-effector includes a sheath and a medical device or needle carrier that is disposed within the interior compartment of the sheath. An aperture is located in a portion of the sheath proximal a distal end of the sheath that is inserted into a natural or artificial cavity. This device is guided by a real-time imager.

26 Claims, 24 Drawing Sheets

Related U.S. Application Data division of application No. 10/512,150, filed as application No. PCT/US03/12253 on Apr. 22, 2003, now Pat. No. 8,244,327.

(60) Provisional application No. 60/374,376, filed on Apr. 22, 2002.

(51) Int. Cl.
| | | |
|---|---|---|
| *A61B 5/055* | (2006.01) | |
| *A61B 5/06* | (2006.01) | |
| *A61B 6/12* | (2006.01) | |
| *A61B 8/08* | (2006.01) | |
| *A61B 10/02* | (2006.01) | |
| *A61B 17/34* | (2006.01) | |
| *A61B 8/12* | (2006.01) | |
| *A61B 17/00* | (2006.01) | |
| *A61B 18/00* | (2006.01) | |
| *A61B 8/00* | (2006.01) | |

(52) U.S. Cl.
CPC ..... *A61B 8/445* (2013.01); *A61B 2017/00274* (2013.01); *A61B 2018/00547* (2013.01); *A61B 2034/107* (2016.02); *A61B 2034/2051* (2016.02); *A61B 2090/365* (2016.02); *A61B 2090/378* (2016.02); *A61B 2090/3784* (2016.02); *A61B 2090/3954* (2016.02); *A61B 2090/3958* (2016.02)

(56) References Cited

U.S. PATENT DOCUMENTS

| | | |
|---|---|---|
| 6,036,649 A | 3/2000 | Yuasa |
| 6,087,831 A | 7/2000 | Bornert et al. |
| 6,400,979 B1 | 6/2002 | Stoianovici et al. |
| 6,425,898 B1 * | 7/2002 | Wilson et al. ............... 606/108 |
| 6,589,190 B2 | 7/2003 | Kanderian, Jr. et al. |
| 6,761,733 B2 * | 7/2004 | Chobotov et al. ........... 623/1.12 |
| 7,918,795 B2 | 4/2011 | Grossman |
| 8,437,833 B2 | 5/2013 | Silverstein |
| 2002/0097050 A1 | 7/2002 | Kellman et al. |
| 2002/0156515 A1 * | 10/2002 | Jang et al. ................... 623/1.11 |
| 2003/0032859 A1 | 2/2003 | Belson |
| 2003/0050557 A1 | 3/2003 | Susil et al. |
| 2003/0083607 A1 | 5/2003 | Bobo |
| 2005/0203413 A1 | 9/2005 | Fichtinger et al. |
| 2005/0288549 A1 | 12/2005 | Mathis |

\* cited by examiner

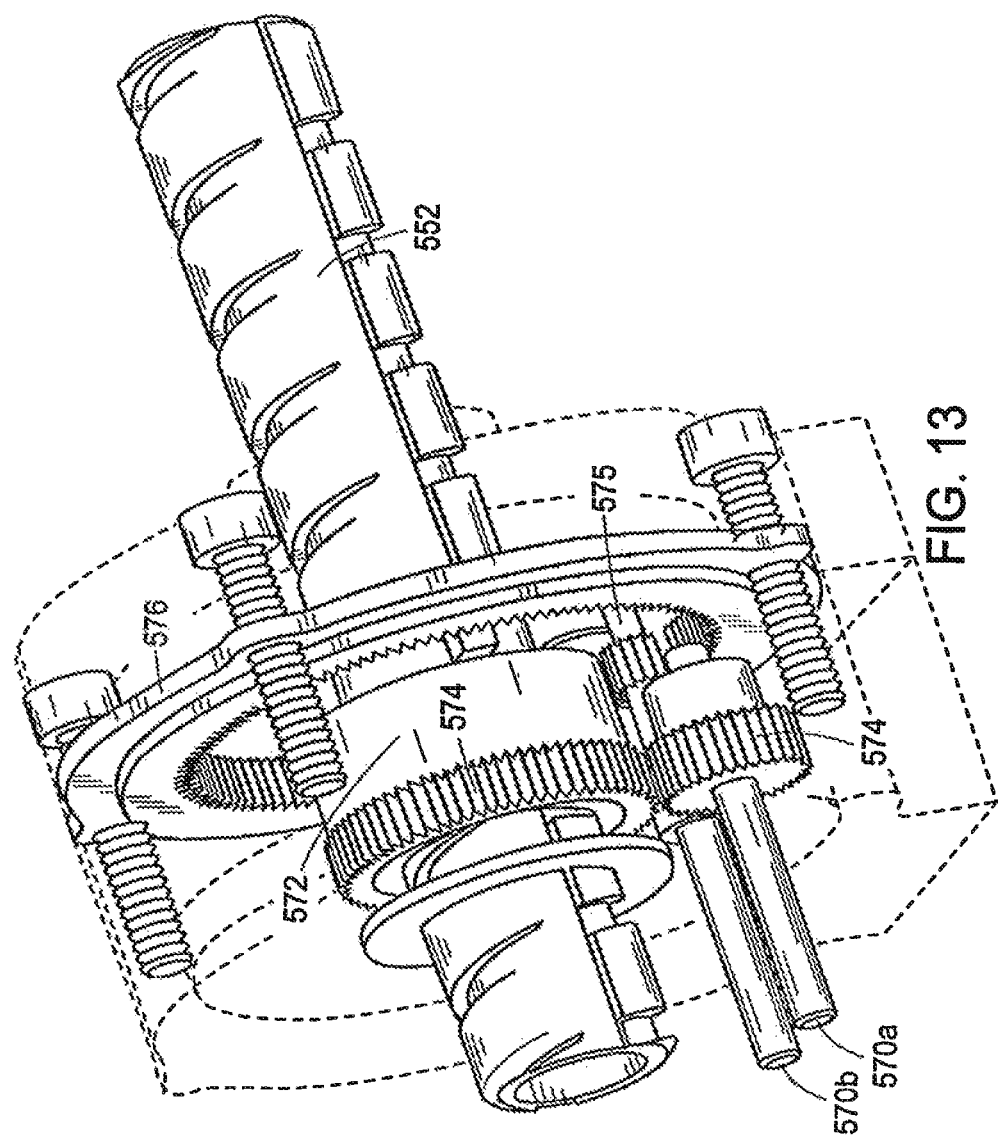

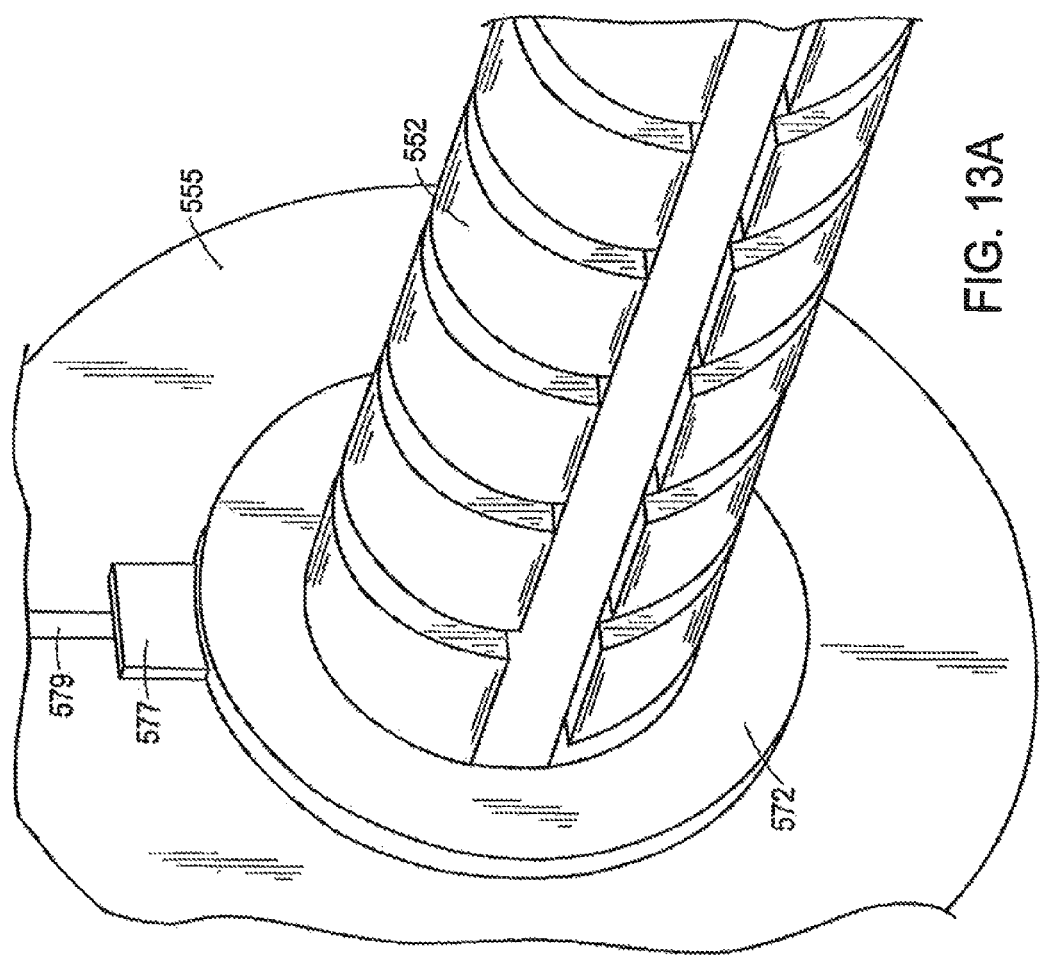

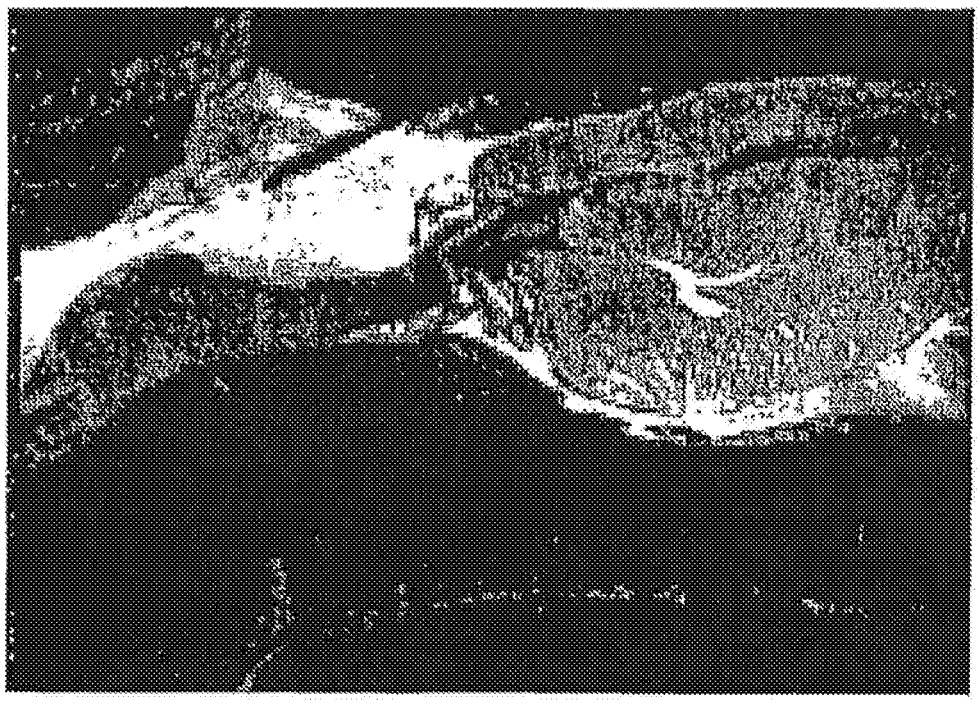
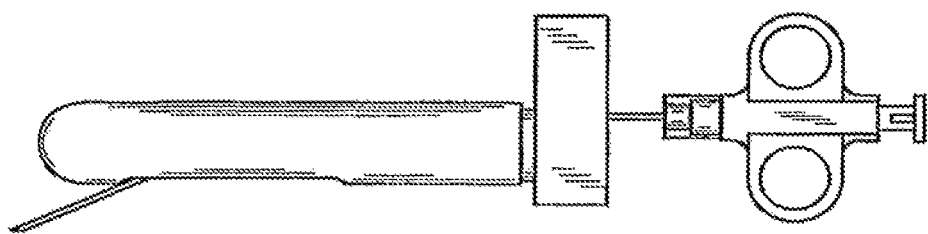
FIG. 17

APPARATUS FOR INSERTION OF A MEDICAL DEVICE DURING A MEDICAL IMAGING PROCESS

CROSS REFERENCE TO RELATED APPLICATIONS

The present application is a continuation of U.S. Pat. No. 8,706,186 filed Jul. 11, 2012, which is a divisional of U.S. Pat. No. 8,244,327, filed on Jan. 30, 2006, which is a 371 National Stage application of PCT/US2003/012253 filed Apr. 22, 2003, which claims the benefit of U.S. Provisional Application No. 60/374,376 filed Apr. 22, 2002. Each of the aforementioned patent applications are hereby incorporated by reference in their entirety.

STATEMENT REGARDING FEDERALLY-SPONSORED RESEARCH

The U.S. Government has provided funding under contract No. grant No. EEC9731478 awarded by the National Science Foundation and thus the government may have certain rights to and/or in the invention.

FIELD OF INVENTION

The present invention generally relates to devices, apparatuses and methods for inserting a medical device such as a needle into a mammalian body while the body is within the imaging field of a medical imager, particularly devices, apparatuses and methods for inserting and guiding a needle to a target site within a body while the body is within the imaging field of a medical imager, and more particularly to devices, apparatuses and methods for inserting and remotely guiding a needle to a target site within a body selected by the user while the body is within the imaging field of a medical imager.

BACKGROUND OF THE INVENTION

Prostate diseases represent a significant health problem in the United States. After cardiac diseases and lung cancer, metastatic prostate cancer is the third leading cause of death among the American men over fifty years, resulting in approximately 31,000 deaths annually. The definitive diagnostic method of prostate cancer is core needle biopsy. Annually in the U.S., approximately 1 million prostate biopsies are performed. The average number of new prostate cancer patients detected by needle biopsy has stabilized around 200,000 per year. Due to the evolution in screening techniques, more cases are diagnosed at an earlier stage, when patients are candidates for some form of minimally invasive localized therapy typically delivered with needles. The majority of the cancer-free biopsied patients are likely to have benign prostate hyperplasia (BPH). Currently more than 10 million American men suffer from BPH. Significant attention has been focused on minimally invasive local therapies of this condition, because its definitive treatment, transurethral resection (TURP) is a highly invasive surgical procedure with potentially adverse side effects. Needle-based ablative therapies have shown promising results lately in the treatment of BPH.

Currently, transrectal ultrasound (TRUS) guided needle biopsy is primary technique being utilized for the diagnosis of prostate cancer [Presti J C Jr. Prostate cancer: assessment of risk using digital rectal examination, tumor grade, prostate-specific antigen, and systematic biopsy. Radiol Clin North Am. 2000 Jan; 38(1):49-58. Review] and contemporary intraprostatic delivery of therapeutics is also primarily performed under TRUS guidance. This technique has been overwhelmingly popular due to its excellent specificity, real-time nature, low cost, and apparent simplicity. At the same time, however, TRUS-guided biopsy fails to correctly detect the presence of prostate cancer in approximately 20% of cases [Norberg M, Egevad L, Holmberg L, Sparen P. Norlen B J, Busch C. The conventional sextant protocol for ultrasound-guided core biopsies of the prostate underestimates the presence of cancer. Urology. 1997 October; 50(4): 562-6; Wefer A E, Hricak H, Vigneron D B, Coakley F V, Lu Y, Wefer J, Mueller-Lisse U, Carroll P R, Kurhanewicz J. Sextant localization of prostate cancer: comparison of sextant biopsy, magnetic resonance imaging and magnetic resonance spectroscopic imaging with step section histology. J. Urol. 2000 Aug; 164(2):400-4].

For the same reason, targeted local therapy today also is not possible with the use of TRUS guidance. Instead, major anatomical regions (or most often the entire prostate gland) are treated uniformly while trying to maintain the fragile balance between minimizing toxic side effects in surrounding normal tissues and providing/giving a sufficient therapeutic dose to the actual cancer. Also importantly, the transrectal ultrasound probe applies variable normal force on the prostate through the rectal wall, causing dynamically changing deformation and dislocation of the prostate and surrounding tissue during imaging and needle insertion, an issue that has to be eliminated in order to achieve accurate and predictable needle placement. The key to successful prostate biopsy and local therapy is accurate, consistent and predictable needle placement into the prostate, and some form of image guidance.

MRI imaging has a high sensitivity for detecting prostate tumors. Unfortunately, MR imaging alone, without concurrent biopsy, suffers from low diagnostic specificity. In addition, there are other fundamental obstacles that must be addressed when using MRI imaging techniques in prostate biopsy and related localized therapy of the prostate. Conventional high-field MRI scanners use whole-body magnets that surround the patient completely and do not allow access to the patients during imaging. Thus, the workspace inside the bore of the whole-body magnet is so extremely limited, that conventional medical robots and mechanical linkages do not fit inside the whole-body magnet. Also, the strength of the magnetic field being generated within the whole-body magnet is about 200,000 times stronger band the magnetic field of the earth. Due to these ultra-strong magnetic fields, ferromagnetic materials and electronic devices are not allowed to be in the magnet due to safety and/or imaging concerns, which excludes the use of traditional electro-mechanical robots and mechanical linkages.

Tempany, D'Amico, et al. [Cormack R A, D'Amico A V, Hata N, Silverman S, Weinstein M, Tempany C M. Feasibility of transperineal prostate biopsy under interventional magnetic resonance guidance. Urology. 2000 Oct. 1; 56(4): 663-4; D'Amico A V, Tempany C M, Cormack R, Hata N, Jinzaki M, Tuncali K, Weinstein M, Richie J P. Transperineal magnetic resonance image guided prostate biopsy. J. Urol. 2000 Aug; 164(2):385-7] proposed to use an open MRI configuration in order to overcome spatial limitations of the scanner. The magnet configuration for this open MRI configuration allows the physician to step inside the magnet and deliver biopsy and therapeutic needles into the prostate. This approach showed that it was possible to use an MRI imaging process to detect cancer previously missed by ultrasound guided needle biopsy and to perform targeted brachytherapy of the prostate. This technique has limitations, however, because it involves the use of an open MRI scanner. Perhaps most importantly, the incurred cost and complexity of open MRI imaging are substantial, especially when compared to transrectal ultrasound imaging.

Open magnets also tend to have weaker magnetic fields than the magnetic fields that are generated using closed magnets, thus open magnets tend to have lower signal-to-noise ratio (SNR) than the SNR for a closed high-field MRI scanners. Consequently, intra-operative images for an open magnet tend to be of a lower quality than the diagnostic images from a closed MRI scanner. While this approach seems to be acceptable when used in a research type of environment, it adds to the complexity and cost of the open MRI. Tempany et al. apply transperineal needle placement for both biopsy and brachytherapy, which is conventionally accepted for therapy, but for biopsy, it is a significantly more invasive route than through the rectum.

Traditionally, needles are placed into the prostate manually while observing some intra-operative guiding images, typically real-time transrectal ultrasound. TRUS biopsy is executed with entirely free hand. Transperineal needle placement is significantly more controlled by stepping transrectal ultrasound and template jigs, however, it still depends on the physician's hand-eye coordination. Therefore, the out comes of TRUS guided procedures show significant variability among practitioners.

Recently, a 6-DOF robot has been presented for transperineal needle placement into the prostate, but that kinematic concept is not applicable in transrectal procedures [G. Fichtinger, T. L DeWeese, A. Patriciu, A Tanacs, D. Mazilu, J. H. Anderson, K. Masamune, R H. Taylor, D. Stoianovici: Robotically Assisted Prostate Biopsy And Therapy With Intra-Operative CT Guidance: Journal of Academic Radiology, Vol 9, No 1, pp. 60-74]. An industrial robot also has been applied to assist TRUS-guided prostate biopsy with the use of a conventional end-shooting probe [Rovetta A, Sala R: Execution of robot-assisted biopsies within the clinical context. Journal of Image Guided Surgery. 1995; 1(5):280-287]. In this application, the robot mimicked the manual handling of TRUS biopsy device in the patient's rectum, in a telesurgery scenario.

A robotic manipulator has been reported for use inside an open MRI configuration, which device is intended to augment the Tempany et al. developed system [Chinzei K, Hata N, Jolesz F A, Kikinis R, MR Compatible Surgical Robot: System Integration and Preliminary feasibility study, Medical Image Computing and Computer-assisted Intervention 2000, Pittsburgh, Pa. Lecture Notes in Computer Science, MICCAI 2000, Springer-Verlag, Vol. 1935, pp. 921-930]. The motors of this robot are situated outside the first magnetic zone, while the motors actuate two long arms to manipulate the surgical instrument in the field of imaging. This solution is not suitable for a closed magnet configuration. In addition, the long arms of this robotic manipulator amplify the effects of flexure and sagging, which can render this system inaccurate for certain procedures. Moreover, because the device is intended to be mounted permanently with respect to the MRI scanner, the robotic manipulator is not flexibly adaptable to different sides of the body.

Recently, a robot has been developed for use inside a conventional MRI scanner that is custom-designed for breast biopsy, [Kaiser W A, Fischer H, Vaguer J, Selig M. Robotic system for biopsy and therapy of breast lesions in a high-field whole-body magnetic resonance tomography unit. Invest Radiol. 2000 Aug; 35(8):513-9]. This robot is mounted on the table of the scanner and it realized six degrees of freedom (6 DOF). This robot is demonstrated in accessing the breast, but it is not readily adaptable for abdominal and intracavity use. There also has been published variations of an in-MRI robot for stereotactic brain surgery, but the actual embodiments of that system also are not applicable in transrectal biopsy [Masamune et. al., Development of an MRI-compatible needle insertion manipulator for stereotactic neurosurgery. Journal of Image Guided Surgery, 1995, 1 (4), pp. 242-248].

Also, multiple investigators have studied tracking of surgical robots and interventional devices in intra-operative medical images. In most imaging environments, passive fiducials are attached to the interventional device in a priori known geometric arrangement, then traces of the fiducials are found in the resulting images [Yao J, Taylor R H, Goldberg R P, Kumar R, Bzostek A, Van Vorhis R, Kazanzides F, Gueziec A. A C-arm fluoroscopy-guided progressive cut refinement strategy using a surgical robot. Comput Aided Surg. 2000; 5(6):373-90; Susil, R. C., Anderson, J. H., Taylor, R. H., (1999) A Single Image Registration Method for CT-Guided Interventions. Lecture Notes in Computer Science, MICCAI99, Springer-Verlag, Vol. 1679, pp. 798-808]. In addition to passive tracking, MRI imaging offers the opportunity to apply micro-coil antennas as active fiducials [Derbyshire J A, Wright G A, Henkelman R M, Hinks R S. Dynamic scan-plane tracking using MR position monitoring. J Magn Reson Imaging. 1998 Jul-Aug; 8(4):924-32]. In this application, the signal processing software "listens" to a prominently present "signature" from the fiducial coils, allowing for accurate real-time calculation of the coil positions.

It thus would be desirable to provide a new device, apparatus, systems and methods for image-guided biopsy and/or a wide range of therapeutic techniques including needle therapy that employs high resolution MRI imaging inside a closed MRI scanner. It also would be particularly desirable to provide such devices, apparatuses, systems and methods for image guided biopsy and/or therapeutic techniques of the prostate, rectum, vagina or cervix, as well as an artificial opening created in the body such as for example those used in connection with laparoscopic procedures/techniques. It would be particularly desirable to provide such a device, apparatus, system and method that would replace the conventional manual technique with a remotely controlled needle insertion and guiding technique to maximize needle placement accuracy and also to minimize dynamic tissue deformation during the procedure. It also would be particularly desirable to provide such devices, apparatuses, systems and methods that employ real-time MRI guidance, are compatible with conventional high-field MRI scanners with no artifact, that can fit inside a closed whole-body magnet and not assume workspace for motion, that can perform needle insertion (e.g., transrectal needle insertion), that minimizes organ motion and deformation in a non-invasive manner and which provides three degree-of-freedom motion to reach a target within the body and selected by the user/medical personnel.

SUMMARY OF THE INVENTION

The present invention features devices, systems, apparatuses and methods for entering a medical device such as a needle into a mammalian body (e.g., a human body), while the body is inside a medical imager such as a MRI scanner, CT, X-ray fluoroscopy, and ultrasound imaging, from within a body cavity (such as the rectum, vagina, or laparoscopically accessed cavity). A minimum three degree-of-freedom mechanical device translates and rotates devices according to the present invention inside the cavity and enters the medical device (e.g., a needle) into the body, and steers the needle to a target point selected by the user. The device is guided by real-time images from the medical imager. Networked computers process the medical images and enable the clinician to control the motion of the mechanical device that is operated remotely from outside the imager.

The devices, systems, apparatuses, and methods of the present invention are particularly adaptable for use in image-guided prostate biopsy that employs high resolution MRI imaging inside a closed MRI scanner, while maintaining safe transrectal access. In addition, such devices, apparatuses, systems and methods embody a remotely controlled needle insertion technique, as compared to the conventional manual manipulation technique, thereby maximizing needle placement accuracy and also minimize dynamic tissue deformation during the procedure. The device, system, apparatus and methods of the present invention also can employ real-time MRI guidance while the system is compatible with high-field MRI scanners with no imaging artifacts. In addition, a device and/or apparatus of the present invention fits inside a closed magnet, assumes very little workspace for motion, minimizes organ motion and deformation in a non-invasive manner and uses at least three degree-of-freedom motion to reach a selected target.

According to one aspect of the present invention there is featured an interventional device for use while a mammalian body is within an imaging field of a medical imaging apparatus. Such an interventional device includes an end-effector member a portion of which is inserted into one of a natural cavity or an artificially formed cavity of a mammalian body while the body is within the imaging field of the medical imaging apparatus. The natural body cavity includes any natural occurring orifice of the mammalian body including the rectum and uterus. An artificial formed body cavity includes those cavities formed as a result of surgical procedures such as laparoscopic surgical procedures.

The end-effector member includes a sheath member having a longitudinally extending interior compartment and a carrier member being one of translatably or rotatably disposed within the sheath member interior compartment. The sheath member also is configured and arranged so it can be received with said one of natural or artificial body cavity. For example, the sheath member is shaped and sized so as to be received in the rectum without causing damage to the tissues thereof. Further, the carrier member is configured and arranged to selectively deploy a medical device therefrom between a stored position and a deployed position. In the deployed position a portion of the medical device is disposed in certain of tissues (i.e., target tissues) about said one of the natural or artificial body cavity. The target tissues include the tissue or cells being targeted for one of diagnosis (e.g., biopsy) or treatment.

More particularly, the sheath member and the carrier member are configured and arranged so rotation and/or translation of the carrier member is not imparted to the sheath member. In this way, and in contrast to prior art devices, the movement of the carrier member does not dynamically change deformation or dislocation of the prostate for example. In more specific embodiments, the carrier member can be selectively translated (e.g., move longitudinally) within the sheath member and then rotated within the sheath member so the carrier member is put into the desired orientation for performing a biopsy, delivering of a therapeutic medium and/or other actions as herein described. In particular embodiments, the sheath member is configured so as to include a through aperture that communicates with the sheath member interior compartment and which extends partially circumferentially and partially longitudinally so as to form a window in an exterior surface of the sheath member. It also is within the scope of the present invention for the medical device to penetrate through or pierce a surface (e.g., end or side surface) of the sheath member as it is being deployed from carrier member to the target tissues.

In more particular embodiments, the end-effector member further includes an imaging device that is configured and arranged so as to image a volume of tissues including the certain tissues. More particularly, the end-effector member further includes an MRI receive antenna, where the MRI receive antenna being configured and arranged so as to image a volume of tissues including the certain tissues. More specifically, the MRI receive antenna is arranged so as to image tissues opposite the sheath member through aperture or opposite an area of a surface the sheath member that the medical device is to penetrate through. In an exemplary embodiment, the MRI receive antenna comprises an MRI coil antenna and wherein said sheath member is configured and arranged so that the MRI coil antenna is disposed about a portion of a perimeter of the sheath member through aperture or a portion of a perimeter of the area of the sheath member surface generally defining an area through which the medical device could penetrate as it is being deployed from the carrier member.

In additional embodiments, the interventional device further includes a positioning mechanism that is operably coupled to the carrier member. This positioning mechanism is configured and arranged so as to one of cause the carrier member to one of translate or rotate within the sheath member interior compartment, more particularly, selectively rotate or translate the carrier member.

In further embodiments, the interventional device further includes a device, mechanism or sub-system that determines one of, or both of, translation or rotation of the carrier member within the sheath member. Additionally, such a device, mechanism or sub-system can further determine an amount of translation and/or rotation of the medical device as it is being deployed.

In particular embodiments, the end-effector member further includes one or more tracking devices, each of said one or more tracking devices being configured and arranged so a position of each tracking device can be determined using an imaging system external to the interventional device. In one exemplary embodiment, the one or more tracking devices are passive fiducials appropriate for the particular imaging technique embodied in the external imaging system and the one or more tracking devices are arranged (e.g., within the carrier member) so as to allow a determination to be made of an amount the carrier member is being translated or rotated within the sheath member.

In more particular embodiments, the end-effector member includes a plurality or more tracking devices. Also, the plurality or more of tracking devices are arranged so as to allow a determination to be made of an amount the carrier member is being translated or rotated within the sheath member.

In another particular embodiment, the interventional device further includes a plurality or more of sensors or sensing devices, that are appropriately coupled to the end-effector and/or positioning mechanism so as to provide one or more outputs, representative of one of, or both of, translation or rotation of the carrier member and/or the medical device as it is being deployed. In more particular embodiments, the plurality or more of sensors include position encoders, incremental encoders, potentiometers or any of a number of other such devices as is known to those skilled in the art which can provide an output of translation rotational motion.

In further embodiments, when the external imaging system is an MRI imaging system and the one or plurality or more tracking devices comprise one of a passive fiducial or a tracking coil. More particularly, one of the passive fiducials or the tracking coils are arranged so as to allow a determination to be made of an amount the carrier member is being translated or rotated within the sheath member. In exemplary embodiments, the end-effector member includes three tracking coils that are arranged so as to allow a determination to be made of an amount the carrier member is being translated or rotated within the sheath member. Such an end-effector member also can include passive fiducials appropriate for tracking the device in MRI images. Reference also shall be made to U.S. Pat. Nos. 5,271,400; 6,470,204 and 6,492,814, the teaching of which are incorporated herein by reference as to further details about tracking coils and the use thereof.

In additional embodiments, the carrier member is configured and arranged so as to include a passage and where the medical device is movably received therein. More particularly, the passage is configured and arranged so an exit thereof is from a surface of the carrier member, more particularly an end or side surface thereof, and a portion of the passage proximal the exit is arcuate. The carrier members also can further comprise a mechanism that is operably coupled to the medical device, where the mechanism is configured so as to rotate the medical device as the medical device traverses at least a portion of the passage. In more particular embodiments, the passage includes a flexible portion proximal the exit and wherein said carrier member further includes a mechanism operably coupled to the passage flexible portion, the mechanism being configured and arranged so as to selectively control one of a position of the exit with respect an exterior surface of the carrier member or an exit angle of the medical device with respect to an axis of the carrier member.

According to further embodiments of the present invention, the interventional device further includes a mechanism for selectively controlling deployment of the medical device from the carrier member into the tissues. The medical device is one of a needle or a flexible needle that is configured to penetrate tissues about the one of natural or artificial body cavity.

Also featured are systems, apparatuses and method related thereto.

Other aspects and embodiments of the invention are discussed below.

DEFINITIONS

The instant invention is most clearly understood with reference to the following definitions:

As used in the specification and claims, the singular form "a", and "the" include plural references unless the context clearly dictates otherwise. For example, the teem "a cell" includes a plurality of cells, including mixtures thereof. The term "a nucleic acid molecule" includes a plurality of nucleic acid molecules.

As used herein, the term "comprising" or "including" is intended to mean that the compositions, methods, devices, apparatuses and systems include the recited elements, but do not exclude other elements. "Consisting essentially of", when used to define compositions, devices, apparatuses, systems, and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients, elements and substantial method steps. Embodiments defined by each of these transition terms are within the scope of this invention.

As used herein, a "target cell" or "recipient cell" refers to an individual cell or cell which is desired to be, or has been, a recipient of exogenous nucleic acid molecules, polynucleotides and/or proteins and includes cells of tissues being targeted by the devices, apparatuses, systems and methods of the present invention. The term is also intended to include progeny of a single cell, and the progeny may not necessarily be completely identical (in morphology or in genomic or total DNA complement) to the original parent cell due to natural, accidental, or deliberate mutation. A target cell may be in contact with other cells (e.g., as in a tissue) or may be found circulating within the body of an organism. As used herein, a "target cell" is generally distinguished from a "host cell" in that a target cell is one which is found in a tissue, organ, and/or multicellular organism, while as host cell is one which generally grows in suspension or as a layer on a surface of a culture container.

As used herein, a "subject" is a vertebrate, preferably a mammal, more preferably a human. Mammals include, but are not limited to, murines, simians, humans, farm animals, sport animals, and pets.

The terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

As used herein, a "composition" refers to the combination of an active agent (e.g., such as a therapeutic agent, nucleic acid vector) with a contrast agent. The composition additionally can comprise a pharmaceutically acceptable carrier or excipient and/or one or more accessory molecules which may be suitable for diagnostic or therapeutic use in vitro or in vivo. The term "pharmaceutically acceptable carrier" as used herein encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin *Remington's Pharm. Sci.,* 15th Ed. (Mack Publ. Co., Easton (1975)).

BRIEF DESCRIPTION OF THE DRAWING

For a fuller understanding of the nature and desired objects of the present invention, reference is made to the following detailed, description taken in conjunction with the accompanying drawing figures wherein like reference character denote corresponding parts throughout the several views and wherein:

FIG. 13 is an illustrative view that illustrates the workings of the positioning stage of the interventional device of FIG. 12;

FIG. 13A is an illustrative view of a portion of the positioning stage of FIG. 12 that embodies another technique for encoding translational and/or rotational positional information;

FIG. 17 is an illustrative view that illustrates placement of the end-effector of the interventional device within the rectum of a canine;

DESCRIPTION OF THE PREFERRED EMBODIMENT

Figure 1:
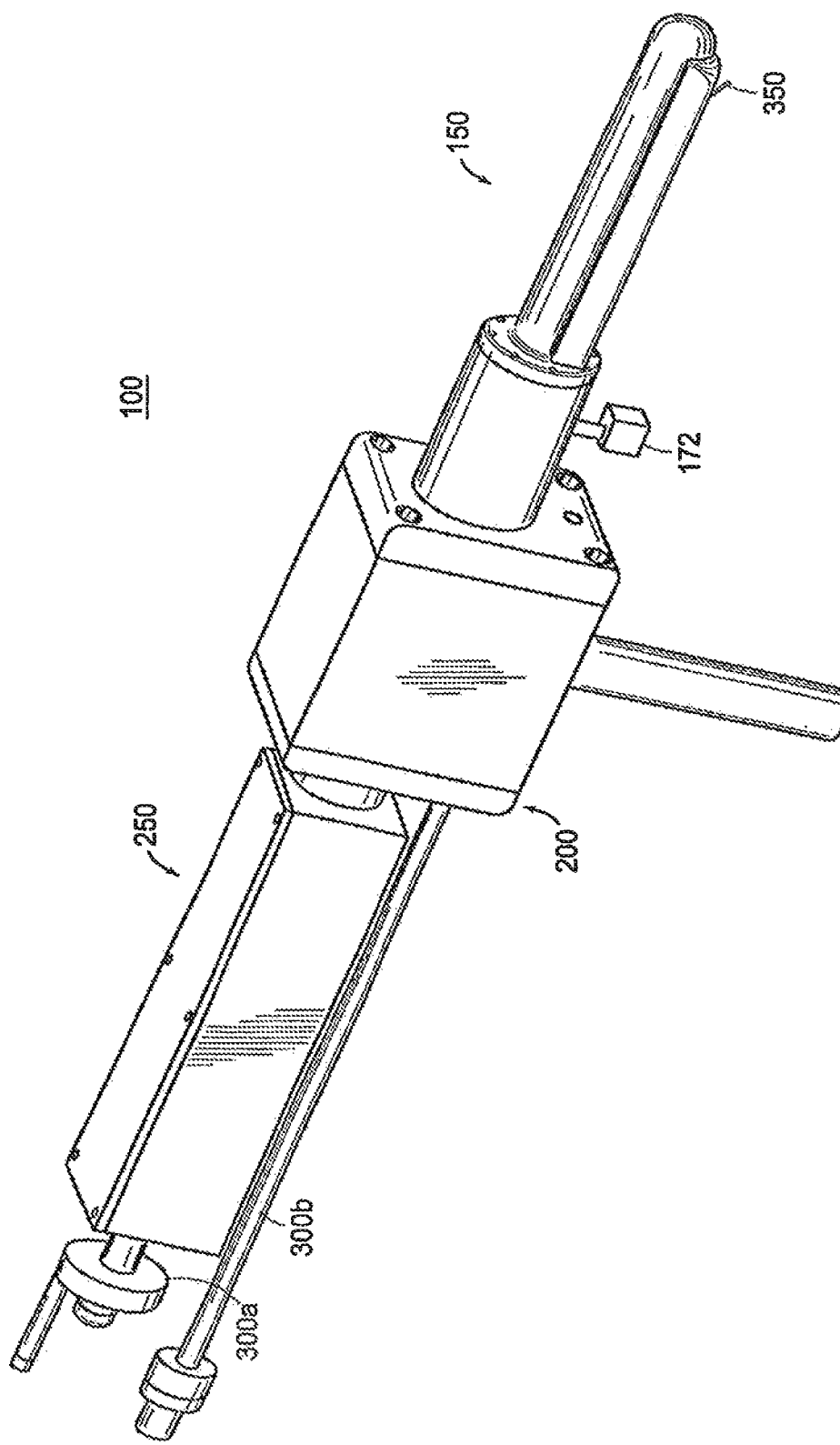
FIG. 1 is an axonometric view of an interventional device according to the present invention.
Figure 2:
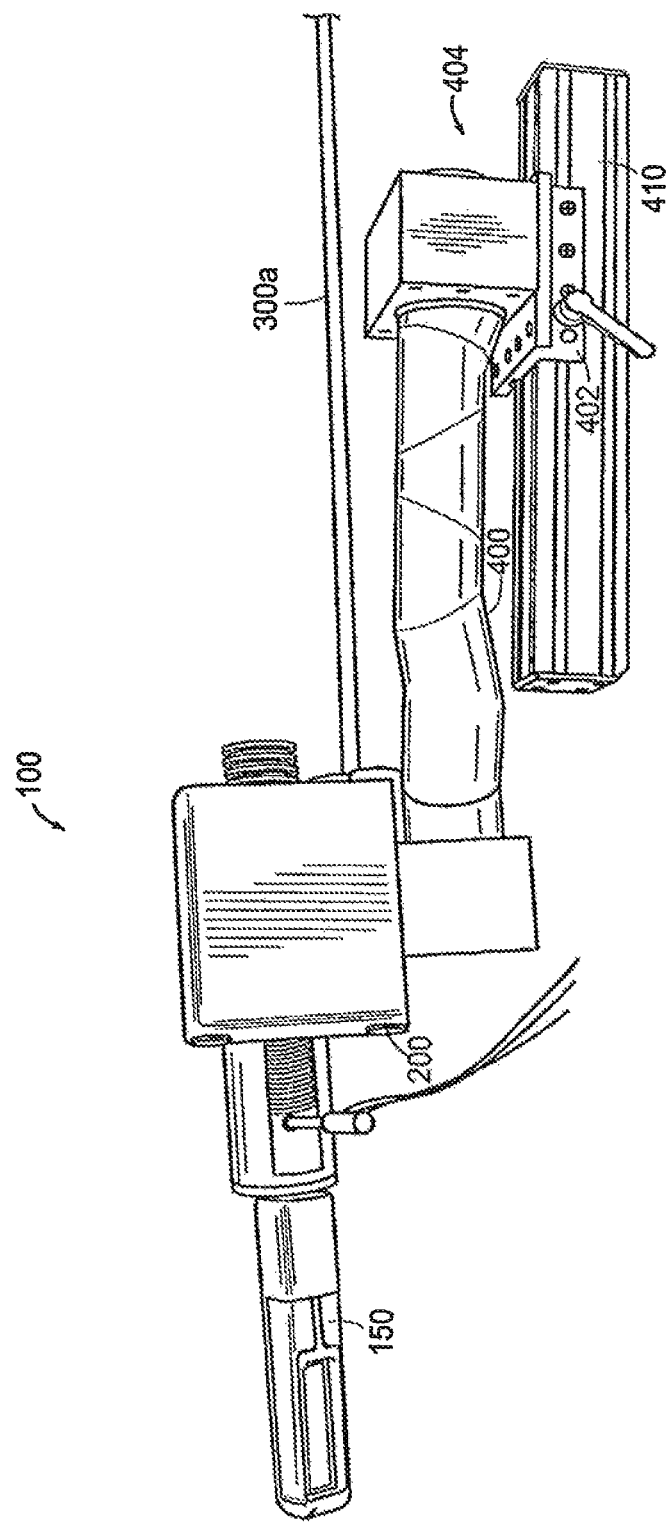
FIG. 2 is a perspective view of an interventional device according to the present invention without an insertion stage for clarity that is affixed to an illustrative positioning apparatus.
Figure 3:
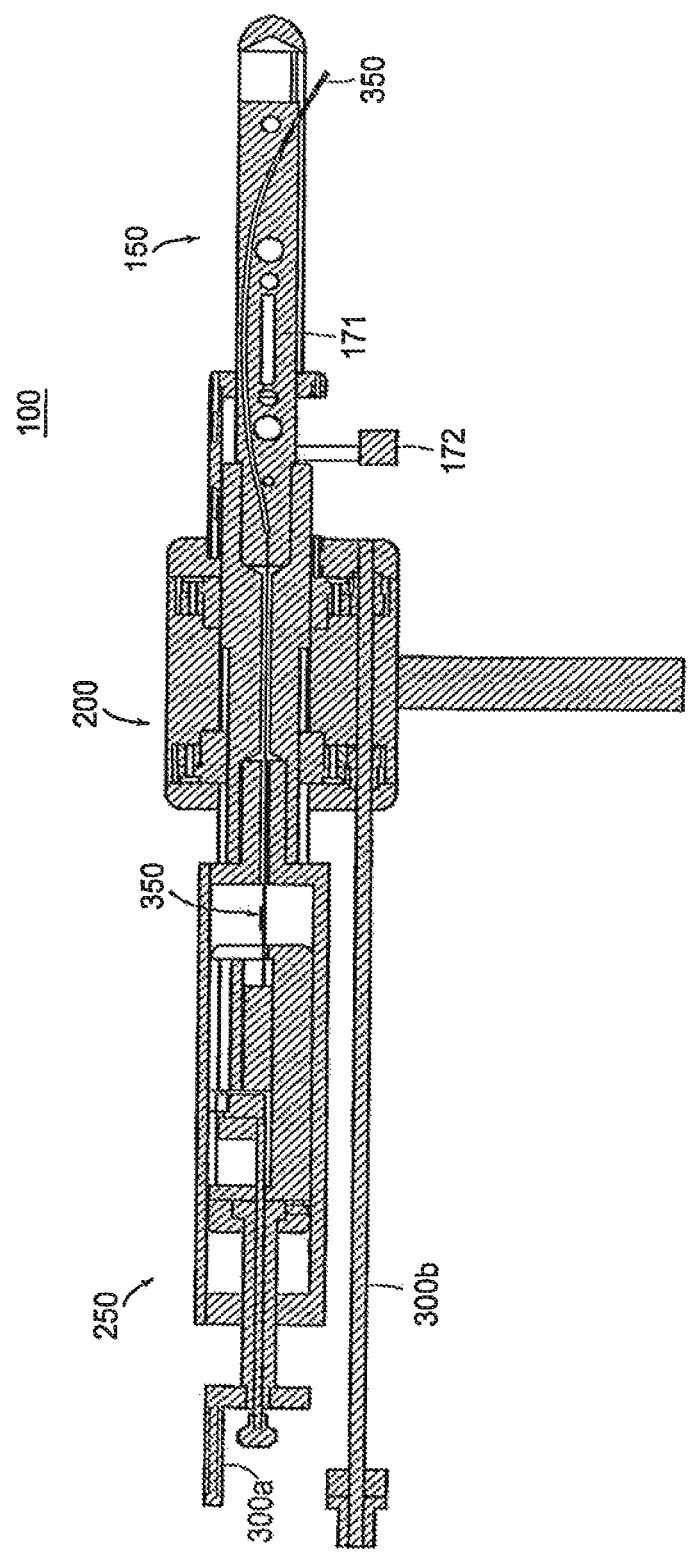
FIG. 3 is a cross-sectional view of the interventional device of FIG. 1.

Referring now to the various figures of the drawings wherein like reference characters refer to like parts, there is shown in FIGS. 1-3 various views of a interventional device 100 according to one aspect of the present invention. In accordance with an embodiment of the present invention, such an interventional device 100 is secured to the table or platform of the scanner or imaging apparatus by affixing or mounting the interventional device to a positioning apparatus 400 as is known to those skilled in that art, such as that illustrated in FIG. 2. The positioning apparatus 400 is any of a number of devices or apparatuses that provide a mechanism for flexible initial positioning of the interventional device 100 as well as securing the interventional device to the table/platform.

The illustrative positioning apparatus 400 includes a slide member 410, a sliding mount 402 and a support arm 404. The slide member 410 is affixed or secured to the table, bed or platform in of the scanner or imaging apparatus. The support arm 404, which in an exemplary embodiment comprises a snake mount, is secured to the sliding mount 402 and to the interventional device positioning stage 200. The sliding mount 402 is slidably disposed or mounted upon the slide member and is configured with a locking mechanism that allows the slide mount to be selectively locked to and unlocked from the slide member.

Such an interventional device 100 includes an end-effector 150, a positioning stage 200, an insertion stage 250 and actuation shafts 300a,b that are operably coupled to the positioning device and the insertion device. Although described in more detail hereinafter, in general terms; the end-effector 150 is introduced into a natural cavity in a subject (e.g., mammalian body), such as for example a rectum or uterus, or an artificial cavity formed in the body such as for example using laparoscopic type of procedures. The positioning stage 200 or the motion stage is operably coupled to the end-effector 150 and provides translation and/or rotation for the end-effector. The insertion stage 250 is operably coupled to the end-effector 150 so as to control the insertion of a medical device such as a needle into the tissues of the target site (e.g., target tissues) such as for example the prostate and its retraction therefrom. The actuation shafts 300a,b are operably coupled to the insertion stage 250 and the positioning stage 200 respectively in such a manner so as to allow for remote operation of the interventional device 100, more particularly the remote operation of each of the insertion stage 250 and the positioning stage 200, from a location that is outside the confines of the scanner/imaging device as well as being outside the field of view of the scanner/imaging device.

It should be recognized that while the interventional device 100 is illustrated with an seriatim ordering of the end-effector 150, positioning stage 200 and the insertion stage 250, this shall not be considered a limitation on the present invention as it is within the skill of any of those knowledgeable in the art to arrange and configure the interventional device so the insertion stage is disposed between the positioning stage and the end-effector as well as arranging the insertion stage so as to be functionally in parallel with the positioning stage.

Figure 4:
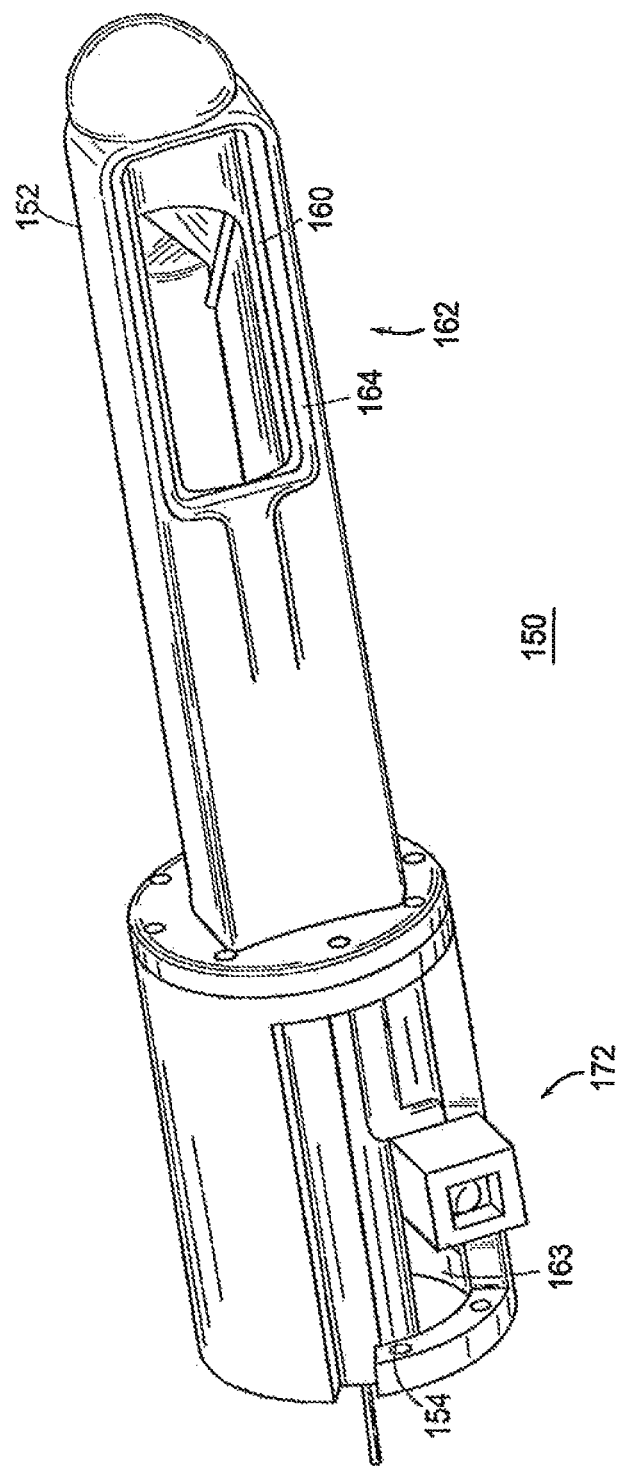
FIG. 4 is an axonometric view of an end-effector of the apparatus of FIG. 1.
Figure 5:
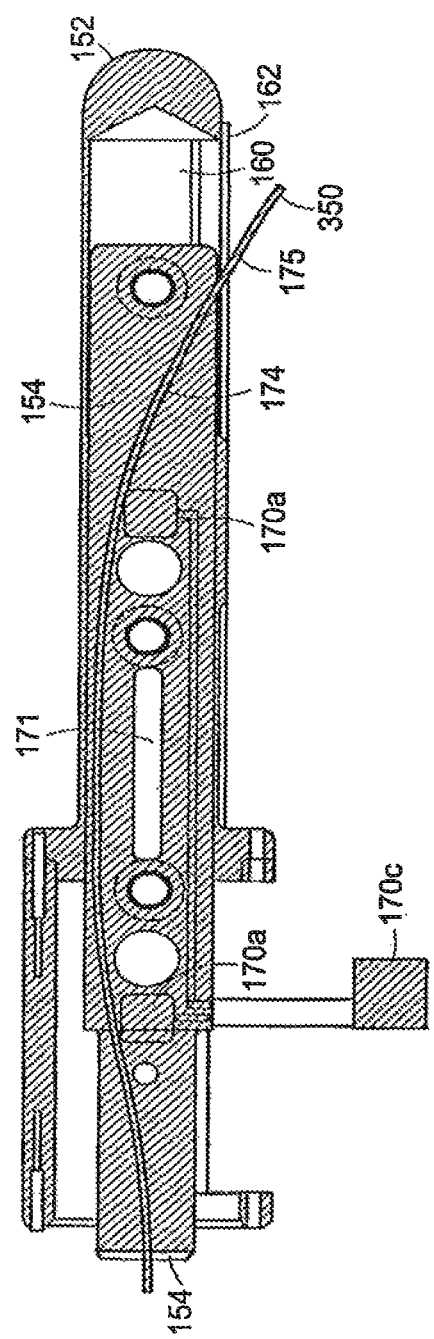
FIG. 5 is a cross-sectional view of the end-effector of FIG. 4.
Figure 6:
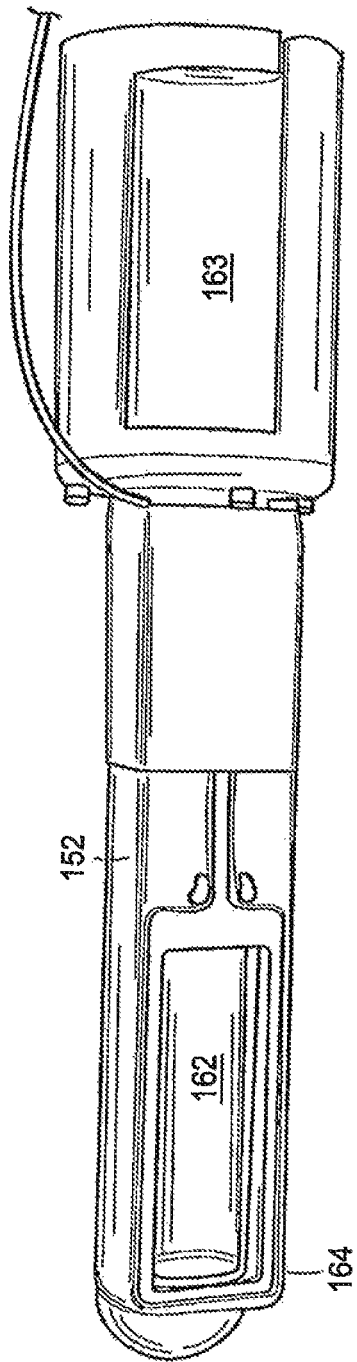
FIG. 6 is an illustrative view of the sheath of the end-effector of FIG. 4.
Figure 7:
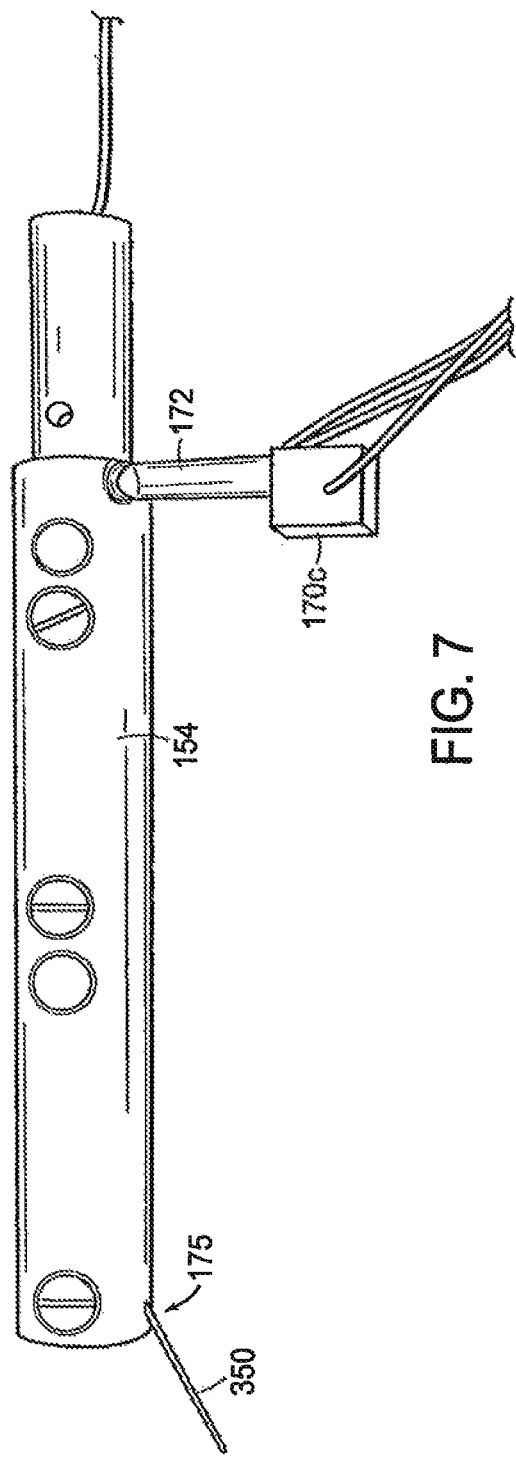
FIG. 7 is an illustrative view of the needle guide of the end-effector of FIG. 4.

Referring now to FIGS. 4-6, there is shown various views of an end-effector 150 according to an embodiment of the present invention that includes a sheath 152 and a medical device or needle carrier 154 that is disposed within an interior compartment 160 of the sheath. Also, the device/needle carrier 154 is disposed within the sheath interior compartment 160 so as to be rotatable and/or translatable along the long axis therein. In an exemplary embodiment, the device/needle carrier 154 is a substantially cylindrical member. In the following discussion the device/needle carrier 154 is referred to as the needle carrier for simplicity, however, this shall not be construed as narrowing the scope of the present invention to this specific example.

The sheath 152 is configured and arranged so as to form a relatively rigid member that minimizes deformation and displacement of the organ during positioning (i.e., during rotation or translation) of the needle carrier 154 and to maintains a generally stationary position with respect to the organ of interest/target tissues. The sheath 152 also is configured so as to include a small window or through aperture 162, which through aperture extends partially about the circumference of the sheath and partially axially along the length of the sheath. In particular exemplary embodiments, the through aperture 162 is located in a portion of the sheath proximal a distal end of the sheath that is inserted into the natural or artificial body cavity. In another embodiment, the through aperture 162 or window is formed in an end surface of the sheath 152.

It also is within the scope of the present invention, and yet another embodiment, for the sheath to be configured and arranged without a through aperture or window. In this embodiment, an area or region of the sheath 152 is designated as an area (hereinafter penetration area) in which the needle 350 penetrates through or pierces a wall (e.g., a side or end wall) of the sheath 152 as the needle is deployed from the carrier member through the exit port 175 to the target site. In further embodiments, the sheath 152, more particularly the penetration area of the sheath, is configured and arranged to facilitate such penetration or piercing by the needle 350. For example, the wall thickness of the sheath 152 in the penetration area is reduced, thereby reducing the force required to be developed for penetration or piercing.

The window or through aperture 162 or the penetration area is configured and sized so as to accommodate a predetermined amount of rotation and translation movement by the needle carrier 154 to locally adjust the exit port 175 for the needle 350 exiting the end-effector 150 with respect to the target site in the target tissues. This provides a mechanism for fine-tuning the location of the needle carrier exit port 175 with respect to the target site without requiring the re-positioning of the sheath 152 in the natural or artificial body cavity. As described herein, the needle 350 exits from the exit port 175 of the needle carrier 154 and passes through the through aperture 162 and thence through the tissues until the end of the needle is positioned at the target site.

In a further embodiment, the sheath further includes a second window or through aperture 163 in which is received an extension member 172 for one of the tracking coils 170c. The second window or through aperture 163 is configured and sized so as to accommodate a predetermined amount of rotation and translation movement by the needle carrier 154 so that the rotational or translational motion of the extension member 172 does not cause the extension member to come into contact with the sides of the second through aperture 163.

Disposed in the sheath 152 and about the perimeter of the first through aperture 162 is an MRI imaging loop antenna 164 that produces real-time anatomic images stationary with respect to the subject anatomy. The MR imaging loop antenna 164 or coil antenna is so arranged such that the volume of tissue that can be imaged by this antenna includes the possible target sites of the needle when it is deployed from the needle carrier 154 into the target tissues. The MRI imaging antenna 164 is sized and otherwise configured as is known by those skilled in the MR arts so that the antenna can image the desired depth that includes the amount the needle can be deployed within the target tissues and with a desired SNR.

The needle guide or carrier 154 is configured and arranged so as to include therein a guide channel 174 that generally extends lengthwise or longitudinally from a proximal end of the needle carrier 154 to the needle exit port 175. In an exemplary embodiment, the guide channel is 174 is sized and configured so as to movable receive therein a flexible standard MRI-compatible 18G biopsy needle. The guide channel 174 can be formed in the structure comprising the needle carrier 154, be a tubular member disposed, mounted/affixed or secured within the needle carrier (e.g., a plastic or Teflon tubular member) or be formed of a combination of such structure and tubular members.

In a preferred embodiment, the needle exit port 175 is positioned in a side surface of the needle carrier 154, although other positions and orientations of the needle exit port 175 are contemplated for use with the present invention, including a needle exit port that is positioned in an end surface of the needle carrier. In this way, the needle 350 generally passes axially through the end-effector 152 via the channel 174 but is re-directed by portions of the channel such that the needle exits through a surface of the needle carrier 154, including a side or end surface thereof, to enter the tissues or the body, for example through the rectum wall when the target tissues are those of the prostate. Consequently, the configuration of the end-effector of the present invention allows the needle exit port 175 to be relatively easily positioned at an ideal location with respect to the target tissues in particular when compared or contrasted with the procedures or techniques followed for conventional devices such as end-shot type of devices. Also, the configuration and methodology of the present invention provides a mechanism by which the needle can be successively steered or directed to a same tissue target location which as indicated herein cannot be readily accomplished with conventional devices or techniques particularly those that use manual manipulation.

In more particular embodiments, the guide channel 174 includes arcuate portions, in particular, the portion of the guide channel 174 that intersects with a wall (e.g., sidewall) of the needle carrier 154 and the needle exit port 175 forms a circular arc. The needle 350 exits the channel 174 via the exit port 175 and follows a straight trajectory tangential to the arc at the point of exit. As also indicated herein, the needle can be rotated as it is being translated through the channel and exiting through the exit port. As explained herein, the angle formed between the needle and the wall (e.g., side or end wall) of the needle carrier is determination using a calibration procedure/methodology according to the present invention.

In an alternative embodiment, the portion of the guide channel 174 proximal the exit port 175 is configured and arranged so as to be flexible and moveable in at last one direction and more particularly in three directions such that the guide channel intersects different locations at least longitudinally and more particularly, angularly and/or longitudinally along the surface of the needle carrier 154. For example, this portion of the guide channel 174 can be in the form of a flexible tubular member. Also, any of a number of mechanisms known to those skilled in the art is operably coupled to the flexible portion to allow the exit port 175 to be selectively re-positioned via manual action or via a remote located device.

In further embodiments, the flexible portion of the guide channel 174 and the mechanism that is operably coupled to the flexible portion are configured and arranged so as to control and adjust the exit angle of the needle 350 with respect to a wall or axis of the needle carrier 154. In this way, the needle 350 can be steered or directed to different target areas without repositioning the exit port 175 or without re-positioning of the needle carrier.

In an illustrative exemplary embodiment, the needle carrier 154 is comprised of two halves that are pinned or otherwise secured together. One half section of the exemplary needle carrier 154 is configured and arranged so as to carry the three registration coils 170a-c that comprise active fiducials, providing the spatial position of the probe in the MRI coordinate system. In this embodiment, two coils 170a,b are positioned along the main axes of the needle carrier 154 and the third coil 170c is positioned at a certain offset of the axes so as to allow registering the rotation of the probe. Reference also shall be made to U.S. Pat. Nos. 5,271,400; 6,470,204 and 6,492,814 the teachings of which are incorporated herein by reference for details as to such MRI active tracking coils. The other half section of the exemplary needle carrier 154 is configured so as to include the guide channel 174 for guiding the needle 350 to the exit port 175.

In more particular embodiments, one or more of the sections of the needle carrier 154 is configured and arranged so as to include one or more passive fiducial channels 171. A material that is appropriate for passively visualizing using a given imaging technique is disposed in the passive fiducial channels 171 or secured in an appropriate fashion to and/or within the carrier guide 154. For example, in the case of imaging techniques embodying MRI techniques, a material comprising an MRI contrast agent such as gadolinium is disposed in the fiducial channel 171. This shall not be limiting as any of a number different kinds and types of passive fiducials can be located in the fiducial channel that is appropriate for the external imaging technique being used to image the tissues and ate least the end-effector 150 of the interventional device 100.

In further embodiments, the interventional device 100 further includes a mechanism that is operably coupled to the needle so as to rotate the needle about the long axis thereof; more particularly rotating about the long axis as the needle is being deployed from the needle carrier 154 to the tissues. Trials have revealed that a needle 350 can be passed though significantly bigger curvatures (e.g., smaller radii of curvatures) by rotating the needle as it passes through a channel 174 with such curvatures while inserting it into the tissues. This rotating insertion distributes elastic deformation equally along a helical path in the needle, resulting in a straight trajectory for the needle. In other words, as the needle is advanced through a needle passage, such as the carrier member channel 174, with simultaneous rotation and translation, the needle will emerge from the passage straight (i.e., with negligible curvature). In the case where the needle 350 is only being translated (i.e., without rotation) through a passage having a small radius of curvature; as the needle passes through the needle passage inelastic bending deformation occurs resulting in the needle emerging from the passage with a repeatable curvature and thus following a non-linear trajectory. Alternatively, such significant curvatures can be used to direct the needle 350 as it exits the needle exit port 175 in a non-linear fashion to a target site.

The sheath 152 and needle carrier 154 are each constructed of any of a number of materials known to those skilled in the art that are biocompatible, appropriate for the intended use and are appropriate for use with the particular imaging technique being utilized for imaging the target tissues. In more particular embodiments, the materials of the sheath 152 and needle carrier 154 are selected so as to minimize the creation of unwanted image artifacts by these components. In exemplary embodiments, the end-effector 150 including the sheath 152 and needle carrier 154 are manufactured from any of a number of biocompatible plastic materials having sufficient strength and rigidity characteristics for the intended use. The MRI loop 164 antenna and the tracking coils 170a-c are made from copper wire or other acceptable material and the needle 350 is made of a material that preferably is non-magnetic and resilient.

Figure 8:
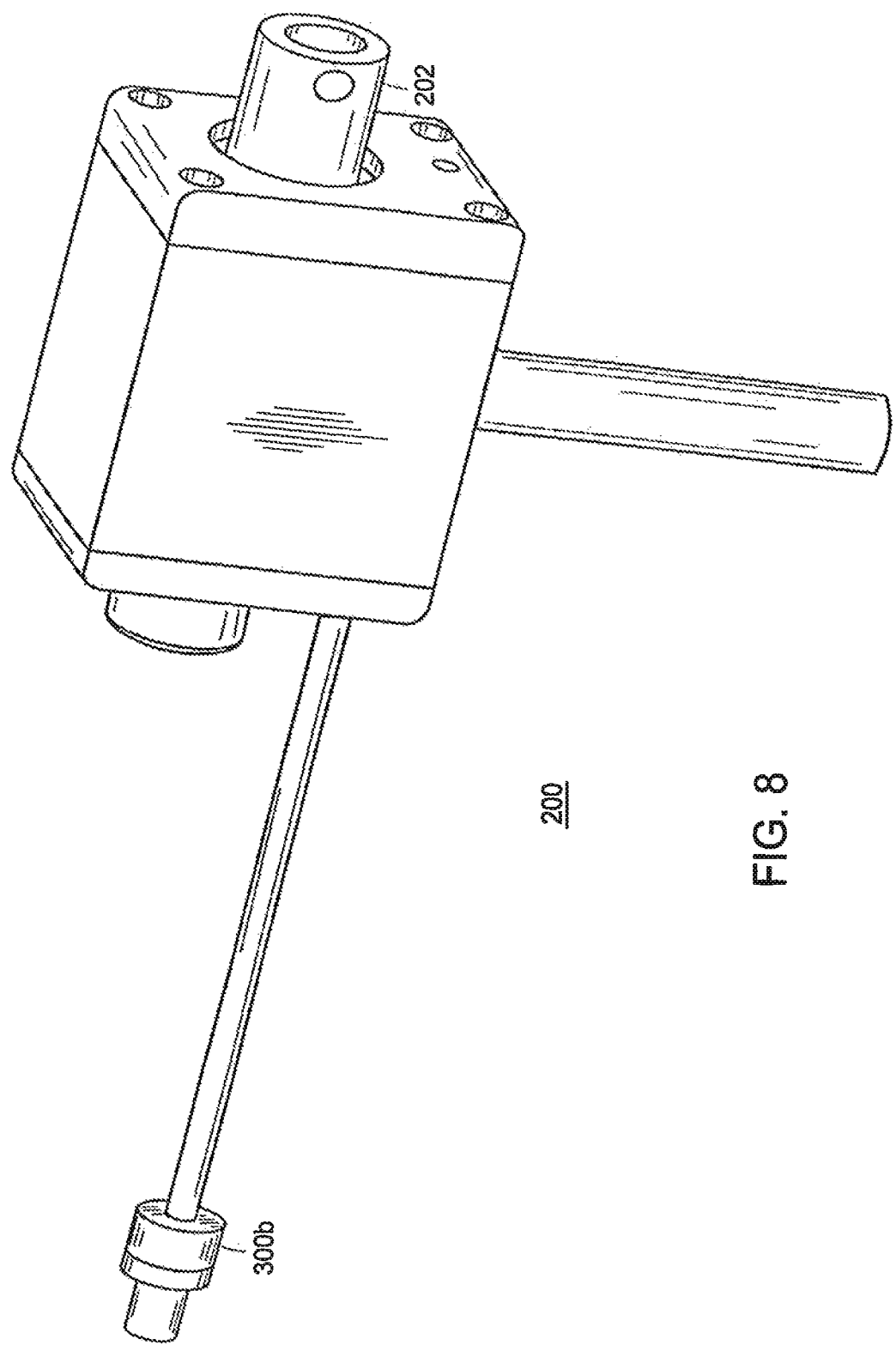
FIG. 8 is an axonometric view of a positioning stage of the apparatus of FIG. 1.
Figure 9:
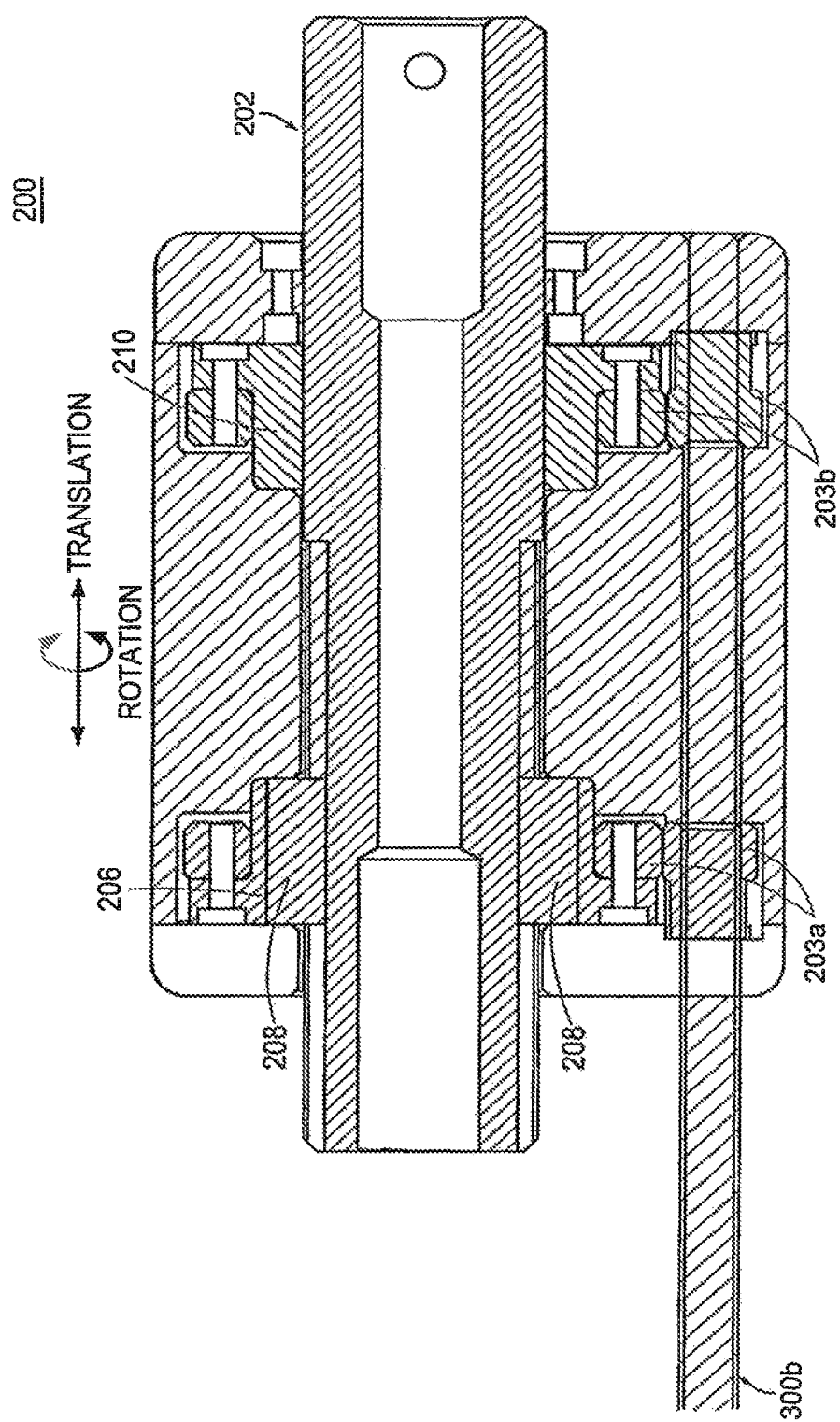
FIG. 9 is a cross-sectional view of the positioning stage of FIG. 8.

Referring now to FIGS. 8-9 there is shown a positioning stage 200 according to one aspect of the present invention that provides the rotation and the translation for the end-effector 150, more particularly the rotation and translation of the needle carrier 154 within the sheath 152. Such rotation and translational motion is communicated to the needle carrier 154 via the main shaft 202 of the positioning stage. The main shaft 202 is operably and mechanically coupled to the needle carrier 154 using any of a number of mechanisms or techniques known to those skilled in the art including the use of pins, screws and an interference fit.

Two concentric shafts 300b are operably coupled to the positioning stage 200 so as to transform rotation of one or more of these shafts into translation and/or rotation of the main shaft 202. In one embodiment, the concentric shafts 300b are manually actuated from outside the gantry of the imaging scanner. In another embodiment, the concentric shafts 300b are coupled to any of a number of drive mechanisms or motors, electrical or hydraulic, as is known to those skilled in the art for remote, selective, and controlled rotation of the concentric shafts.

In exemplary embodiments, the concentric shafts 300b are coupled so as to act over a gear reduction. 203a,b to turn two separate nuts 206, 210 that are engaged with the main shaft 202. The rotation nut 206 connects to the main shaft 202 through two splines 208 that run in a linear groove of the shaft, providing the rotation of the main shaft. The translation nut 210 is a threaded nut that engages threads of the main shaft 202. Thus, rotation of the translation nut 210 thereby provides the translation of the main shaft 202.

The positioning stage 200 also includes a housing 212 that in an illustrated embodiment includes a block and two lids. The housing 212 rotatably supports the main shaft 202 and also restricts the rotation and translation nuts 206, 210 from translating which as is known to those skilled in the art causes the main shaft to translate and/or rotate responsive to rotation of the respective nut(s). The housing block also includes an attachment member that is secured to a universal mount such as that illustrated above in FIG. 2.

In one embodiment, the positioning stage 200 and the components thereof are constructed of any of a number of materials known to those skilled in the art that are appropriate for use with the particular imaging technique being utilized for imaging the tissues as well as being appropriate for the intended use. In more particular embodiments, the materials are selected so as to minimize the creation of unwanted image artifacts by these components. In exemplary embodiments, the materials include any of a number of plastics known to those in the art that are appropriate for the intended use (e.g., having sufficient strength and rigidity characteristics for the intended use).

In as much as the interventional device 100 is typically arranged so that the positioning stage 200 is not in the field of view of the medical imaging apparatus; or is at least outside the first zone of the MRI imaging device, it is within the scope of the present invention that in alternative embodiments other materials, for example non-magnetic materials such as aluminum, brass, titanium and the like to be used for one or more of the components comprising the positioning stage. For example, the meshing gears comprising the gear reduction or the rotational or translation nuts can be made of such non-magnetic materials thereby allowing part sizes to be reduced because of the strength characteristics of such materials as compared to typical medical grade plastics.

Figure 10A:
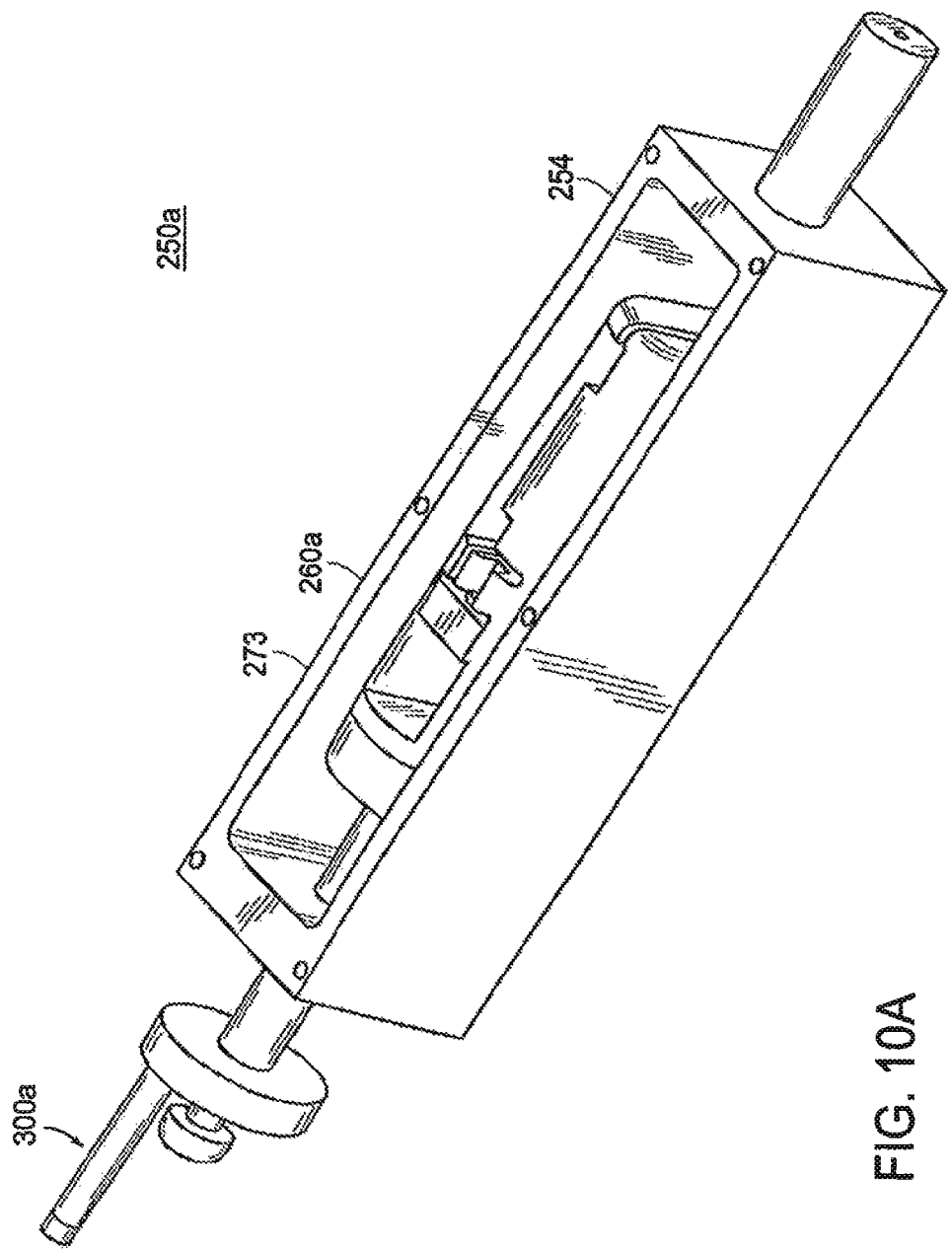
FIG. 10A is a perspective view of one embodiment of the insertion stage with cylindrical cartridges.
Figure 10B:
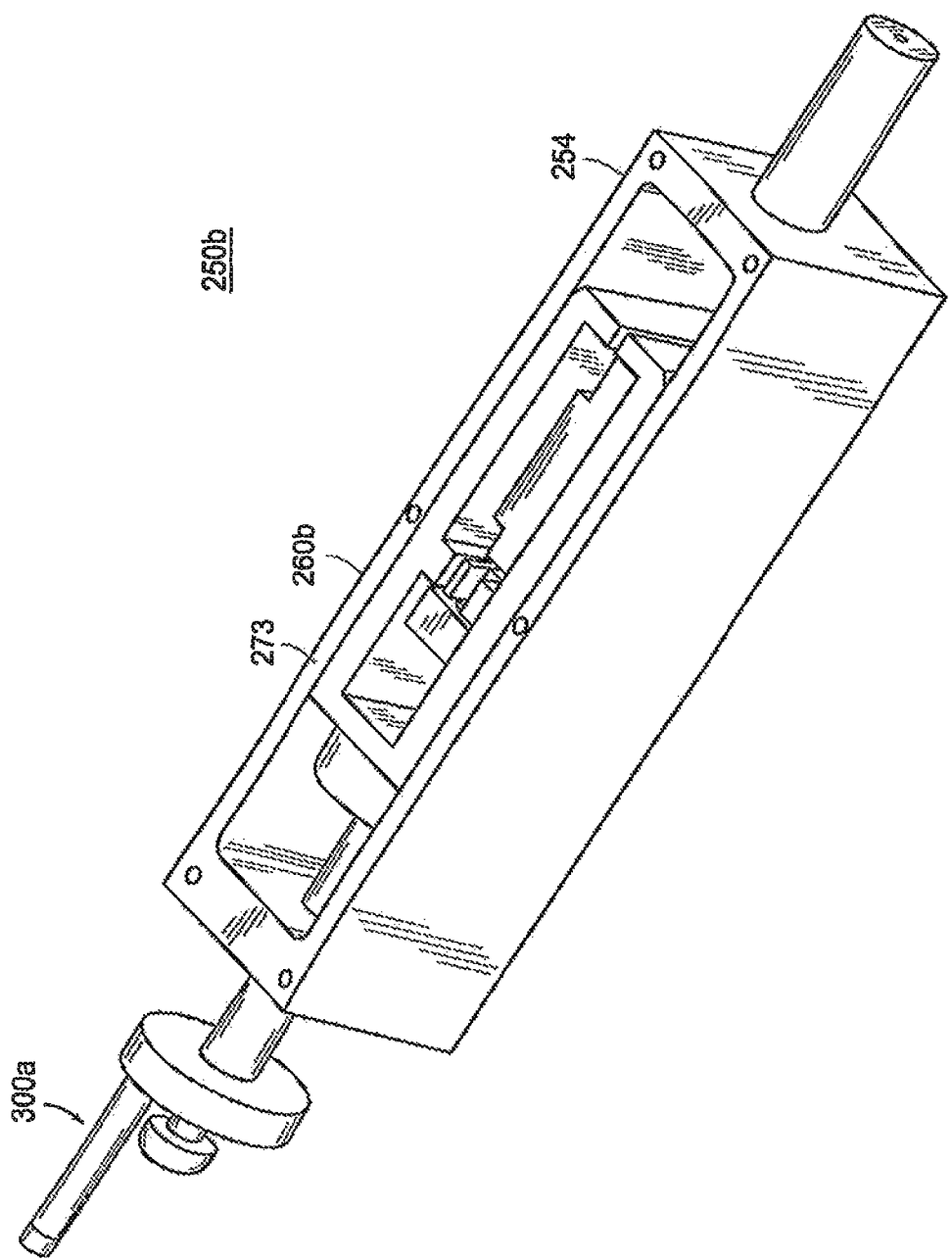
FIG. 10B is a perspective view of another embodiment of the insertion stage with quadratic cartridges.
Figure 11:
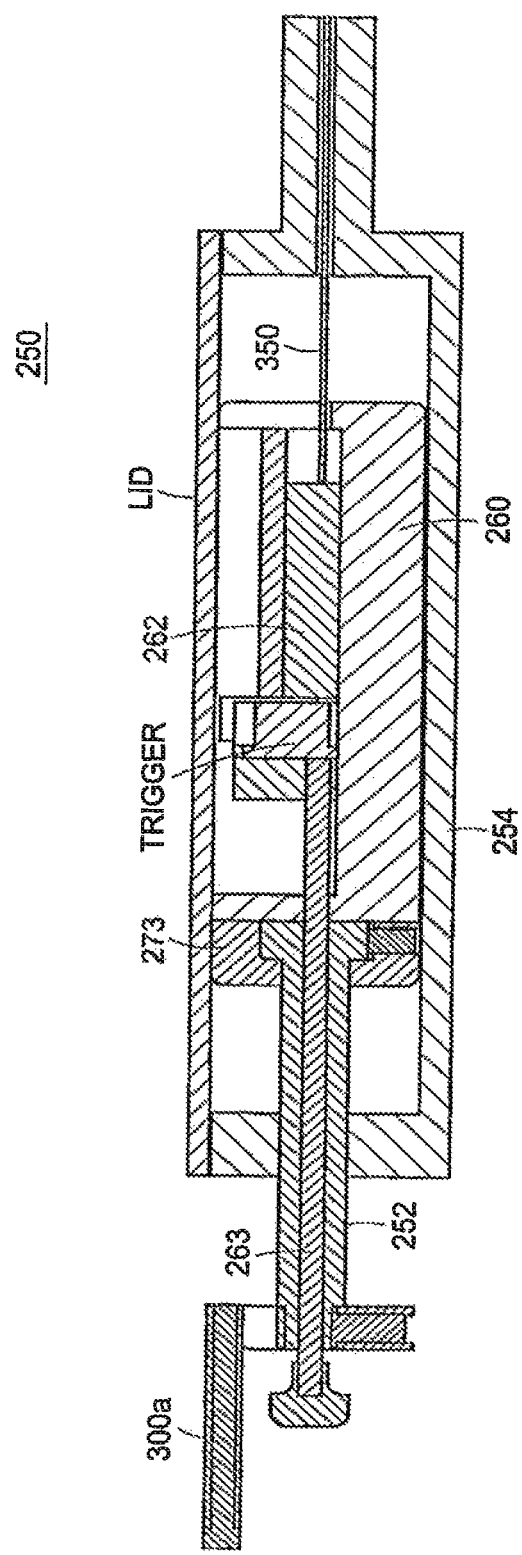
FIG. 11 is a cross-sectional view of the insertion stage of FIG. 10A.

Referring now to FIGS. 10-11 there is shown various views and embodiments of an insertion stage 250 according to the present invention. As indicated above, the needle insertion stage 250 is configured and arranged so as to deploy the needle from the needle carrier 154 and to insert the needle to a predetermined depth in the tissues and also to retract the needle from the tissues after completing the biopsy or treatment process. The insertion stage 250 transforms rotation of a knob affixed to another actuation shaft 300a into a well-defined insertion of the needle 350 to a predetermined target depth and also actuates the shooting mechanism of a biopsy gun. In an exemplary embodiment, a 18G standard prostate biopsy needle (Daum Gmbh, Schwerin, Germany) was adapted for use.

The knob turns a lead screw 252 that engages a thread in a block 254 of the insertion stage 250. The coupling transfers movement of the screw into the cartridge 260, which runs in a pocket of the block and carries the biopsy gun 262. Switching between a round cartridge 260a (FIG. 10A) or a square cartridge 260b (FIG. 10B) and tightening or loosening a setscrew on the coupling 273 allows for either a rotating insertion or a pure translating insertion of the needle 350. As indicated above, rotating insertion allows a needle to be passed through significantly larger curvatures than in the case where non-rotating insertion is performed. In addition, some studies have indicated that rotating insertion also assists the needle in penetrating the tissues at the entrance site and within the body thereby minimizing or reducing insult (see also US Patent Publication No. 2002/0111634, the teaching of which are incorporated herein by reference). Such reduction is particularly advantageous in cases where multiple needle insertions are contemplated. In the case where the insertion stage 250 is configured to perform biopsy, a push-pull plunger 263 actuates the biopsy gun 262 by loading and firing the gun.

In other embodiments, the insertion stage is configured and arranged so as to allow access to the proximal end of the needle 350 that is located outside of the subject. In use, the user can insert any of a number of medical devices, therapeutic mediums or compositions, imaging devices and the like through the lumen of the needle 350 and into the target site of the target tissues. For example, a loopless MRI imaging antenna can be passed along the length of the needle so as to more directly image the tissues at or about the target site.

Markers or seeds can be passed though the needle lumen and deposited within the tissues at or about a target site to facilitate localization of the tissues within target site. Thus, and for example, medical personnel can use such markers or seeds to provide a more accurately identified location for therapeutic treatment for example by a beam therapy technique. Such seeds or markers themselves also can comprise a source of radiotherapy as well as devices that provide long-term and controlled release of therapeutic compounds of chemotherapeutic agents to the tissues. The foregoing is illustrative of a few medical techniques and procedures that can be used in combination with the interventional device 100 of the present invention so as to provide diagnostic and/or therapeutic treatment.

Because such materials, agents and medical devices are introduced outside the field of view of the imaging apparatus, the medical personnel need not have significant access to the bore of the main magnet. Also, because the medical devices and the like are not present within the field of view while imaging the tissues before treatment the medical devices and the like do not present a concern with the generation of a problematic image artifact. Finally, the medical device and the like can be configured and arranged so that it can be imaged using the desired imaging technique (e.g., MRI) after the medical device or the like have been inserted or localized to the target site of the target tissues.

In the case where therapeutic agents are to be administered to the tissues or cells at or about the target site, the insertion stage 200 can include a syringe, a syringe pump or other mechanism or device known to those skilled in that art that is fluidly coupled to the proximal end of the needle 350. In use, the therapeutic medium or other fluid is thereby injected through the needle lumen 350 by such syringe, syringe pump or other such mechanism or device.

In one embodiment of the present invention, the insertion stage 250, more particularly the components thereof except the push-pull plunger 263 are made from a material that is appropriate for the imaging process and for not creating image artifacts. In an exemplary embodiment, when MRI comprises the imaging technique, the insertion stage 250 including the constituents thereof except for the push-pull plunger, and the medical devices, delivery, devices and the like coupled to the proximal end of the needle, are made from plastics. In an illustrative embodiment, the push-pull plunger is made from aluminum or other non-magnetic materials when MRI is the imaging technique. The push-pull plunger 263 is located sufficiently far from the field of view of the imaging apparatus so as to not cause a measurable signal distortion. In as much as the interventional device 100 is typically arranged so that the insertion stage 250 is not in the field of view of the medical imaging apparatus; it is within the scope of the present invention for other materials, for example non-magnetic materials such as aluminum, brass, titanium and the like to be used for one or more of the components comprising the insertion stage.

Figure 12:
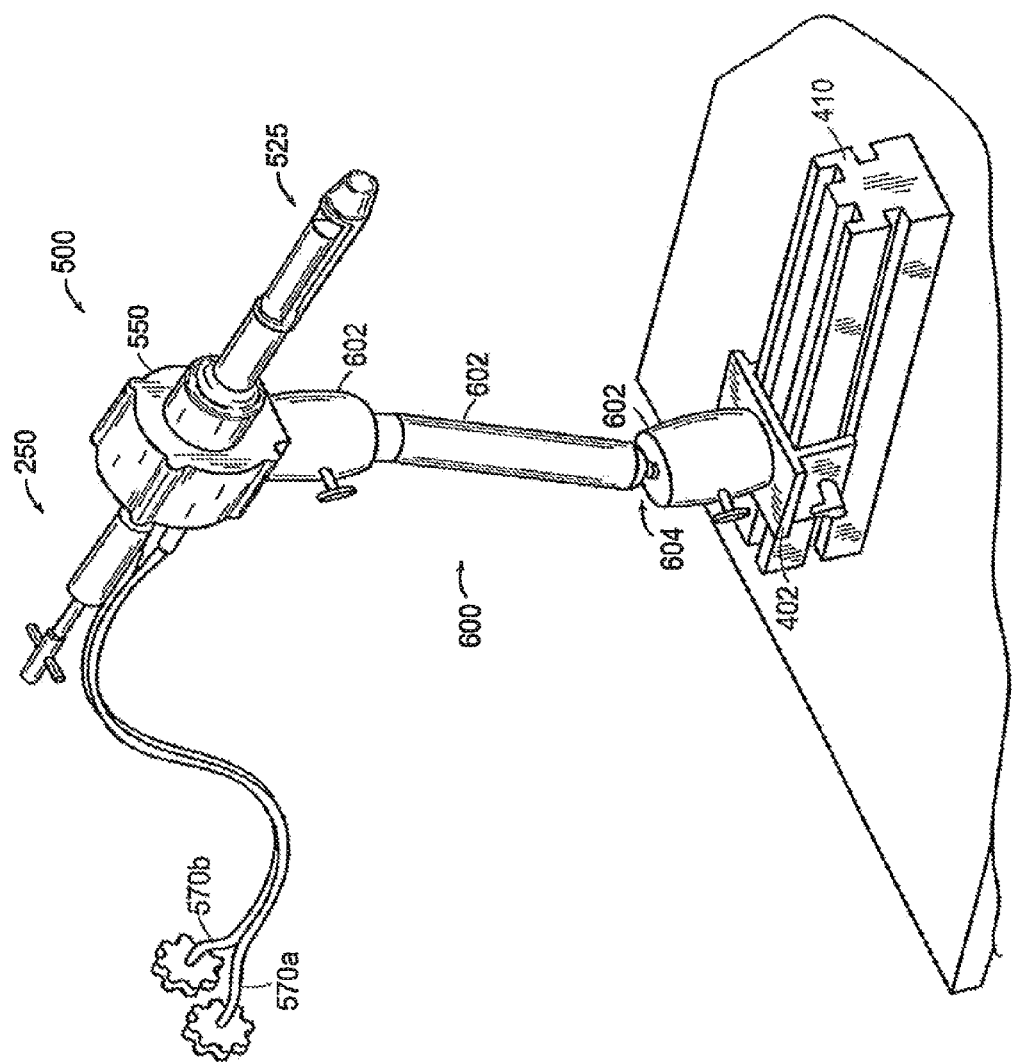
FIG. 12 is a perspective view of an interventional device according to another aspect of the present invention affixed to another illustrative positioning apparatus.

Referring now to FIGS. 12-13 there is shown an interventional device 500 according to another aspect of the present invention that is secured to another illustrative positioning apparatus 600. The illustrated positioning apparatus 600 includes a plurality of segments 602 that are interconnected to each other by one of a plurality articulated joints 604. The articulated joints 604 are of the type that can be selectively loosened and tightened for example by the tightening of a screw or bolt. One of the segments 602 is connected to a slide mount 402 and another of the segments 602 is in connected to the interventional device positioning stage. Reference shall be made to the discussion above for FIG. 2 as to further details for the slide mount 402 and the slide member 410. As is known to those skilled in the art, the plurality of segments 602 and articulated joints 604 in combination with the sliding mount 402 and the slide member 410 of the positioning apparatus 600 provide a mechanism for flexible initial positioning of the interventional device 500 as well as securing the interventional device to the table, bed or platform of the scanner or imaging apparatus.

The interventional device 500 includes an end-effector 520, a positioning stage 550 and an insertion device 250, where reference shall be made to the above discussion regarding FIGS. 4-7 and 10-11 for further details of the insertion device and the end-effector not otherwise provided below. In this embodiment, the end-effector 550 differs from that described above in that the within embodiment does not include an extension member 172 that extends outside of the sheath 552 and the internally located components of the needle carrier 554 have been arranged so as to reduce the cross-section of the sheath and the needle carrier.

The positioning stage 550 of this embodiment includes two flexible shafts 570a,b that have actuation elements (e.g., knobs, motors, and the like) that are located remote from the field of view of the imaging apparatus. The flexible shaft 570a for controlling translation motion of the needle carrier is coupled to a nut 572 via gear reduction 574 such that rotation of the flexible shaft in turn causes the nut to rotate over a gear reduction 574. The nut 572 is threaded and threadably engages the main shaft 552, which is threaded. Thus, as the nut 572 rotates, such rotation drives the main shaft in a translational motion.

The other flexible shaft 570b is connected to a small gear 575, which engages an internal gear 576. The internal gear 576 is held stationary by the housing of the positioning stage 550. Consequently, rotation of the small gear 575 causes the entire inner assembly including the actuation shafts 570a,b and the main shaft 552 to rotate.

In the foregoing discussion, the mechanisms and methods described for tracking the rotational and/or translational movement of the needle carrier uses an external imaging apparatus for locating the tracking devices. It is within the scope of the present invention for an interventional device according to the present invention to embody any of a number of positional tracking devices, apparatuses, systems and methods as is known to those skilled in the art. In an exemplary embodiment, and with reference to FIG. 13A, there is shown a portion of a positioning stage 550 of FIG. 12 including any one of a number of devices known to those skilled in the art, that allow a position to be determined, such devices include optical encoders, incremental encoders, position encoders and potentiometers.

In the illustrated embodiment, an encoder 577 is positioned or mounted to the housing 555 of the positioning stage proximal the nut 572 that causes translation motion of the main shaft 552. The encoder is configured and arranged so as to measure the rotation of the translation nut 572, and thus provide an output signal representative of the translation of main shaft 552. In an exemplary embodiment the encoder is an optical encoder or a potentiometer. In this way, the amount of rotation of the translation nut 572 can be equated to amount of translation of the main shaft 552 and thus an amount of translation of the carrier member 154. The encoder 577 or encoder device is operably coupled via a cable 579 to instrumentation and/or devices positioned external to the field of view of the imaging apparatus that provide a remote indication to the user of the amount of translation.

Similarly, an encoder or other position determining device can be placed within the positioning stage housing 555 and appropriately positioned so as to measure the rotation of the main shaft 552. Further, the needle 350 can be configured so as to include a mechanism, for example a code strip affixed to the needle that could be used in conjunction with an encoding or position determining device to determine an amount of translation of the needle and thereby an amount of insertion of the needle into the tissues.

Reference also should be made to the foregoing discussion as to FIGS. 1-11 as to the positioning stage, the insertion stage and the end-effector as to the materials and other construction details.

Figure 14:
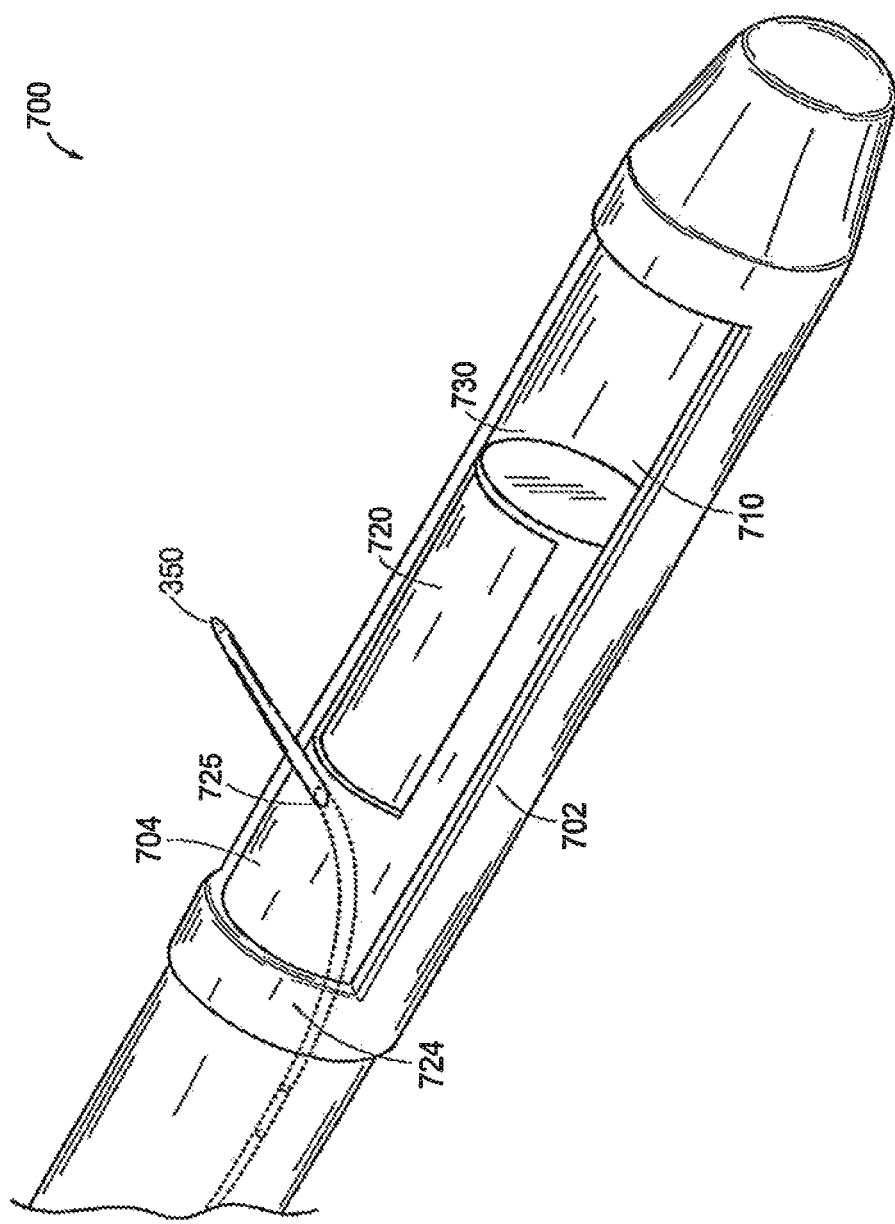
FIG. 14 is a perspective view of an end-effector according to the present invention configured to use ultrasound for imaging of the target tissues.

In the interventional devices 100, 500 hereinabove described, after insertion of the end-effector into the subject, the target tissues are imaged using an MRI imaging loop antenna or coil 164. Referring now to FIG. 14, there is shown an end-effector 700 according to another aspect of the present invention that can be used in combination with the positioning stages 200, 550 or the insertion stage 250 as described herein.

The end-effector 700 includes a sheath 702 and a medical device or needle carrier 704 that is disposed within an interior compartment 730 of the sheath. Also, the device/needle carrier 704 is disposed within the sheath interior compartment 730 so as to be rotatable and/or translatable along the long axis therein. In an exemplary embodiment, the device/needle earner 704 is a substantially cylindrical member. In the following discussion the device/needle carrier 704 is referred to as the needle carrier for simplicity, however, this shall not be construed as narrowing the scope of the present invention to this specific example.

The sheath 702 is configured and arranged so as to form a relatively rigid member that minimizes the deformation and displacement of the organ during positioning (i.e., during rotation or translation) of the needle carrier 704 probe and to maintains a generally stationary position with respect to the organ of interest/target tissues. The sheath 702 also is configured so as to include a small window or through aperture 710, which through aperture extends partially about the circumference of the sheath and partially axially along the lengthwise of the sheath. In particular exemplary embodiments, the through aperture 710 is located in a portion of the sheath proximal a distal end of the sheath that is inserted in the natural or artificial body cavity. As also indicated herein, in further embodiments, the sheath 702 can be configured and arranged so as to include a penetration area or penetration region instead of the through aperture 710.

The window or through aperture 710 or the penetration area is configured and sized so as to accommodate a pre-determined amount of rotation and translation movement by the needle carrier 704 to locally adjust the exit port 725 entrance site for the needle 350 exiting the end-effector 700 with respect to the target site in to the target tissues. This provides a mechanism for fine tuning the location of the needle carrier exit port 725 with respect to the target site without requiring the re-positioning of the sheath 702 in the natural or artificial body cavity. As described herein, the needle 350 exits from the exit port 725 of the needle carrier 704 and passes through the through aperture 710 and thence through the tissues until the end of the needle is positioned at the target site.

The needle guide or carrier 154 is configured and arranged so as to include therein a guide channel 724 that generally extends lengthwise or longitudinally from a proximal end of the needle carrier 704 to the needle exit port 725. In an exemplary embodiment, the guide channel is 724 is sized and configured so as to movable receive therein a flexible standard needle. The guide channel 724 can be formed in the structure comprising the needle carrier 704, be a tubular member disposed, mounted/affixed or secured within the needle carrier (e.g., a plastic or Teflon tubular member) or be formed of a combination of such structure and tubular members.

In a preferred embodiment, the needle exit port 725 is positioned in a side surface of the needle carrier 704, although other positions and orientations of the needle exit port 725 are contemplated for use with the present invention, including a needle exit port positioned in an end surface of the needle carrier 704. In this way, such that the needle 350 generally passes axially through the end-effector 700 via is led through the channel 724 but is re-directed by portions of the channel such that the needle exits through a surface, a side or end surface, of the needle carrier 704 to and finally enters the tissues or the body, for example through the rectum wall when the target tissues are those of the prostate. Consequently, the configuration of the end-effector 700 of the present invention allows the needle exit port 725 to be relatively easily positioned at an ideal location with respect to the target tissues in particular when compared or contrasted with the procedures or techniques followed for conventional devices such as end-shot type of devices. Also, the configuration and methodology of the present invention provides a mechanism by which the needle can be successively steered or directed to a same tissue target location which as indicated herein cannot be readily accomplished with conventional devices or techniques particularly those that use manual manipulation.

In more particular embodiments, the guide channel 724 includes arcuate portions, in particular, the portion of the guide channel 724 that intersects with the sidewall of the needle carrier 704 and the needle exit port 725 forms a circular arc. The needle 350 exits the channel 724 via the exit port 725 and follows a straight trajectory tangential to the arc at the point of exit. As also indicated herein, the needle 350 can be rotated concurrent with translation through the channel. As explained herein, after assembly of the needle carrier, the angle formed between the needle and sidewall of the needle carrier is determined using a calibration procedure/methodology according to the present invention.

In an alternative embodiment, the portion of the guide channel 724 proximal the exit port 725 is configured and arranged so as to be flexible and moveable in at last one direction and more particularly in three directions such that the guide channel intersects different locations at least longitudinally and more particularly, angularly and/or longitudinally along the side surface of the needle carrier 704. For example, this portion of the guide channel 724 can be in the form of a flexible tubular member. Also, any of a number of mechanisms known to those skilled in the art is operably coupled to the flexible portion to allow the exit port 725 to be selectively re-positioned via manual action or via a remote located device.

In further embodiments, the flexible portion of the guide channel 174 and the mechanism that is operably coupled to the flexible portion are configured and arranged so as to control and adjust the exit angle of the needle 350 with respect to a wall or axis of the needle carrier 154. In this way, the needle 350 can be steered or directed to different target areas without repositioning the exit port 175 or without re-positioning of the needle carrier.

The needle carrier 704 also is configured and arranged so as to include an ultrasound crystal 720 that is arranged so as to image a volume of tissues that includes the tissues of the target site and the tissues in which the needle would be disposed if deployed from the needle carrier in a given position. The ultrasound crystal is any of a number of ultrasound crystals known in the art and appropriate for the intended use, including those crystals and devices embodying crystals such as those used in connection with transrectal ultrasound guided needle biopsy and low permanent seed brachytherapy procedures.

The sheath 702 and needle carrier 704 are each constructed of any of a number of materials known to those skilled in the art that are biocompatible, appropriate for the intended use and are appropriate for use with the particular imaging technique being utilized for imaging the target tissues. In more particular embodiments, the materials of the sheath 702 and needle carrier 704 are selected so as to minimize the creation of unwanted image artifacts by these components. In exemplary embodiments, the end-effector 700 including the sheath 702 and needle carrier 704 are manufactured from any of a number of a biocompatible plastic materials having sufficient strength and rigidity characteristics for the intended use.

Although the mechanism for imaging the tissues of the target site after an interventional device including an end-effector 700 according to this aspect of the present invention is ultrasound, it is within the scope of the present invention for other imaging techniques, including CT and MRI techniques to be used, to determine the initial position of the interventional device as well as any imaging occurring concurrent with and following post treatment or diagnostic procedures. As such, it is within the scope of the present invention for the needle carrier 704 according to this aspect of the present invention to include passive and/or active fiducials to assist such other imaging systems in imaging and determining the location of the end-effector within the subject or body.

Figure 15:
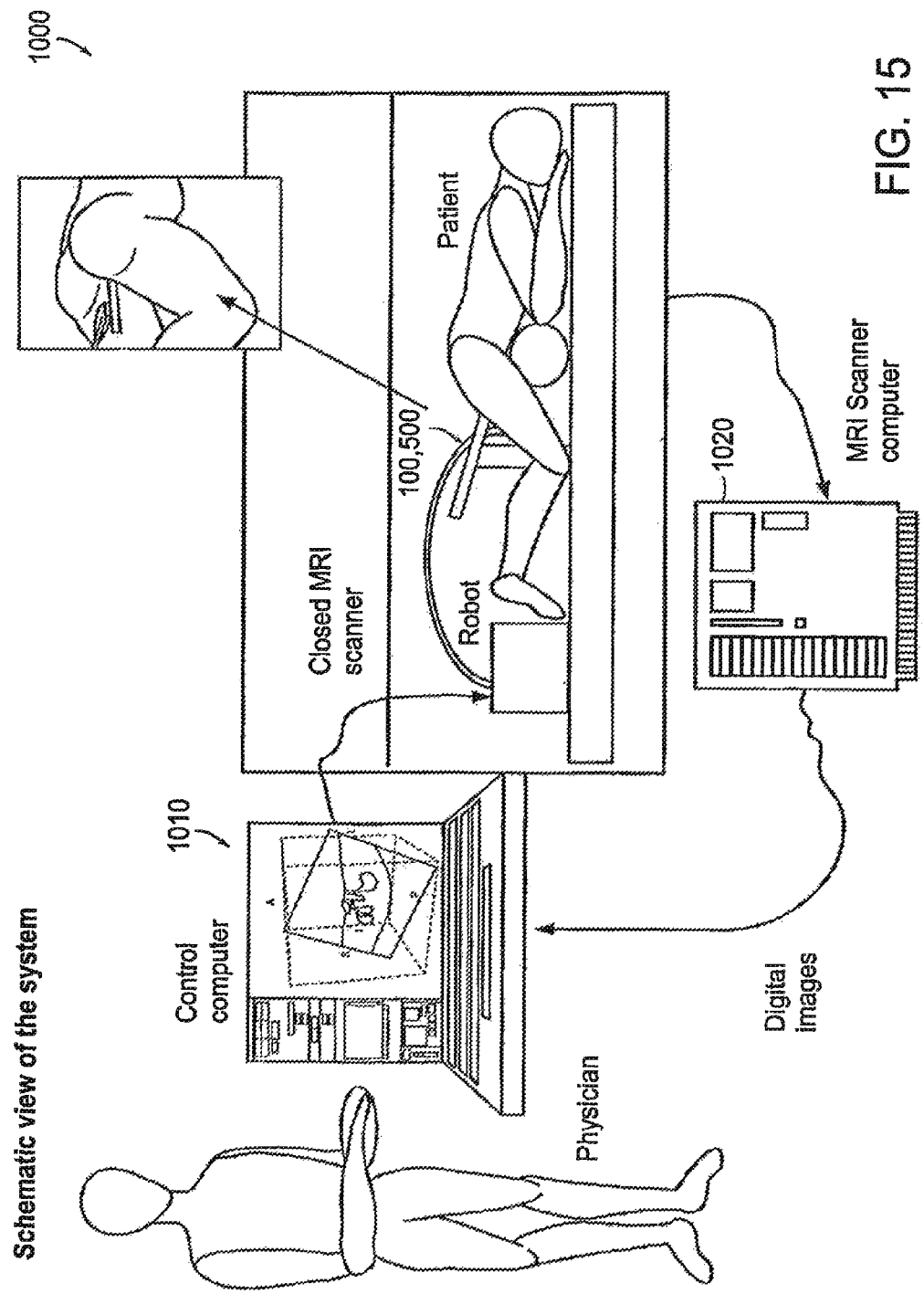
FIG. 15 is a schematic view of an interventional system according to the present invention.
Figure 16:
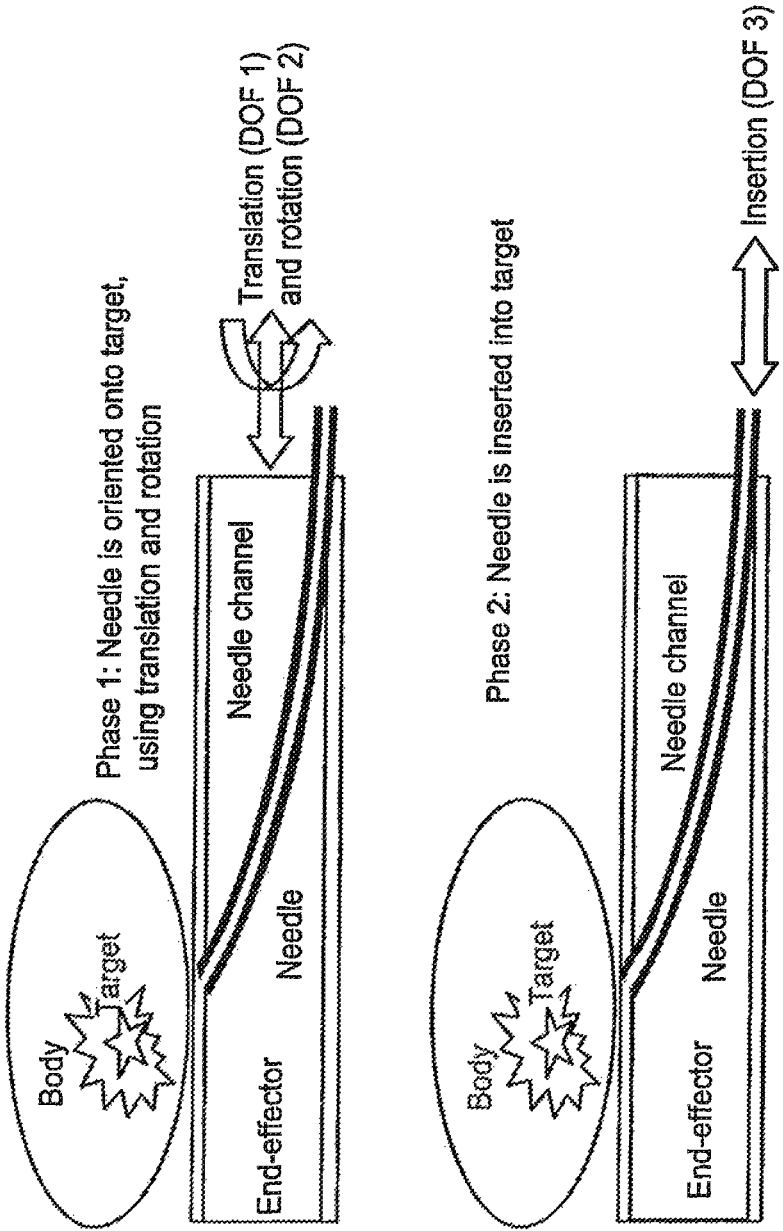
FIG. 16 is an illustration of the targeting methodology when using three degrees of freedom.

The use of the interventional devices 100, 500 of the present invention as well as related systems, apparatuses and methods can be best understood from the following discussion along with FIGS. 15-17. Reference shall be made to the foregoing discussion regarding FIGS. 1-14 for other details and features not otherwise described hereinafter. For purposes of discussion, the following describes the use of such an interventional device in connection with biopsy and treatment procedures for the prostate including accessing the prostate via the rectum. This shall not be construed as limiting the device and related systems, methods and apparatuses to this particular application. It is contemplated that the interventional devices 100, 500 of the present invention as well as related systems, apparatuses and methods can be adapted for use in connection with a wide range of diagnostic and/or treatment procedures for accessing the male prostate and surrounding tissues via the rectum, accessing tissues of the female body through the vagina and cervix and accessing body tissues via a laparoscopic portal. Such accommodation for such different applications can be achieved for example, by appropriate re-configuring and sizing the end-effector 150, 525 to fit the requirements of a given application.

A system 1000 according to the present invention is shown in FIG. 15. Prior to the surgical, diagnostic or treatment procedure, and while the patient is still outside the gantry, the interventional device 100, 500 is secured to the table, bed or platform of the scanner or imaging apparatus with an adjustable mounting mechanism such as the exemplary positioning apparatuses 400, 600 described herein. The adjustable mounting mechanism or positioning mechanisms 400, 600 allow flexible positioning of the interventional device 100, 500 with respect to the subject or patient as herein described.

In order to achieve an initial position, the adjustable mounting mechanism is unlocked. The subject or patient is positioned comfortably on the platform, bed, table or couch of the scanner or imaging apparatus in a prone body position with their pelvis slightly elevated as is illustrated. The interventional device 100, 500 is adjusted so its end piece, the end-effector 150, 525 is aligned with the rectum. The end-effector 150, 525 of the device is inserted into the rectum, in same way as transrectal ultrasound probes are used for brachytherapy implants. The end-effector sheath 152, which is attached about the needle carrier 154, makes contact with the rectum, thus leaving the needle carrier rotatable and translatable inside the sheath. The sheath prevents the needle carrier 154 from causing mechanical distortion to the rectum wall and prostate while it is moving inside the rectum. After a satisfactory initial position is achieved, the adjustable mount is secured to hold this position. Using the sliding table of the scanner, the patient and interventional device are moved into the bore of the scanner's magnet.

The MRI scanner produces signals with the subject or patient and device in the field, at the same time. Using signal processing tools, the spatial relationship between the interventional 100, 500 device and the coordinate system of the MRI scanner is determined. The MRI images are transferred onto a computer 1010 that produces three-dimensional graphical representation of the interventional device superimposed on anatomic images. The physician or medical personnel interacts with the display and selects the target point for the needle 350 (e.g., target point for the tip of the needle). The computer 1010 calculates the coordinate transformation to guide the needle carrier 154 and the needle 350 from its current position to the selected target position. In other words, the computer 1010 determine how much to rotate and/or translate the needle carrier 154 from its present position to a final position where the needle exit port 175 is at a location for deployment of the needle 350 and how much to insert the needle so the needle (e.g, the tip of the needle) will arrive at the three-dimensional coordinates corresponding to the target location.

It should be recognized that the interventional device of the present invention allows a surgeon or medical personnel to image the needle carrier 154 using the active and/or passive fiducials during such rotation and translation to dynamically adjust for any changing conditions as well as to verify that the needle carrier has rotated and/or translated the desired amount before the needle is deployed or inserted into the tissues of the subject. In addition, the surgeon or medical personnel can image the tissue volume including the target tissue site to verify that the needle has been deployed to the intended target location. Consequently, the devices, systems and methods of the present invention, allow a surgeon or medical personnel to determine the parameters to control movement of the end-effector 150 and needle 350 so as to reach a target site within a subject and to verify placement or deployment of the needle to the desired target site before a biopsy is taken or treatment is undertaken.

It should be recognized that the foregoing could not be readily accomplished using conventional procedures, techniques and devices. Such conventional techniques, devices and systems typically involve manual manipulation of an end-shooting type of device so that the end of the device is pointed at the volume of tissue including the target site. Because the needle and imaging device (e.g., ultrasound crystal) are at the end of the device, the surgeon or medical personnel have to push against the subjects rectum and/or anus in such a way so the body of the device is positioned within the rectum so the end is pointed in the desired direction. In other words, for conventional devices, systems and techniques, the body of the device being inserted into the rectum cannot be aligned with the rectum for insertion. In addition to creating the potential pain to the subject at least following the procedure, the process increases the risk of damage, trauma or insult to rectal tissues. In addition, because there is no practical way using conventional devices, methods and systems, to pre-determine and maintain direction or the position of the device end with respect to the target site, the user cannot determine precisely how much to move the device from a given location to a final position before a needle is inserted.

It is contemplated that the interventional device 100, 500, methods and systems of the present invention are to work with or embody computational image guidance techniques. In this case, fiducial markers with known geometric distribution are incorporated with the end-effector 150, 525, preferably in a pre-established arrangement. Images are acquired with the interventional device and patient/subject together in the field of view of the scanner or imaging apparatus. The digital images are transferred from the scanner to the planning computer 1010 via local area network or other suitable connection. The fiducial marks leave traces in the images, from which the planning computer 1010 calculates the location and orientation of the end-effector 150 with respect to the imager. The operator/user selects the target within the prostate for example on the computer screen and the computer 1010 calculates the location of the target with respect to the imager. Using a priori geometric information of the end-effector 150, the computer 1010 determines the spatial relationship between the current and the intended positions of the device.

The computer 1010 calculates three parameters for controlled motion: translation length for the end-effector 150, rotation angle for the end-effector, and insertion length for the needle 350. The program displays this information to the user, who can actuate the interventional device 100, 500 accordingly. The three stages of motion are kinematically decoupled in the interventional device and thus can be executed sequentially. This enables the user to acquire new image upon completing a phase of the motion and determine whether the sequence of motions was calculated and executed correctly. The above described image guidance mechanism is equally applicable with MRI, CT, X-ray, and ultrasound imaging.

As indicated above, in the present invention, three imaging coils 170*a-c* are situated in the end-effector 150 of the interventional device 100. Each imaging coil winds around a small capsule containing gadolinium solvent, in order to provide a strong signal in the vicinity of the coil. Two coils 170*a-b* are located in the central axis of the end-effector 150, to encode translational motion of the interventional device, more particularly translational motion of the needle carrier 154. The third imaging coil 170*c* is located off central axis, in order to encode rotation around the central axis. As also indicated herein, the interventional device of the present invention can be configured so as to include one or more devices or sensors as is known to those skilled in the art that can determine translational and/or rotational motion of the carrier member without the use of an external imaging apparatus. Such a position determining sub-system can be used alone or in combination with the external imaging apparatus to ascertain an amount of rotational and/or translational motion of the carrier member.

Thus, the computer 1010 computes the kinematic sequence for the individual motion stages: the length of translation of the end-effector (i.e., the needle carrier) inside the rectum, the degree of rotation of the end-effector (i.e., the needle carrier) inside the rectum, and the depth of insertion for the needle 350. The order of translation and rotation are interchangeable, but both are completed before the needle 350 is inserted into the tissues. Referring now also to FIG. 16 there is shown a schematic view of the end-effector and the method of targeting with the a 3-DOF interventional device such as that of the present invention. The computer 1010 can also simulate the sequence by moving the graphical model of the interventional device being displayed, so that the physician or medical personnel can verify that the calculated sequence of motion would take the needle 350 from its current position to the pre-selected target position. As indicated above, the computer 1010 also displays the three motion parameters to the operator.

There also is illustrated in FIG. 17 positioning of an end-effector within the rectum of a canine as well the deployment of the needle from the needle carrier into the tissues. This generally illustrates that the imaging technique can visualize the needle 350 and the end-effector 150 after the needle is deployed and the position of the needle with respect to tissues and/or organs of the subject.

According to another embodiment, the methodology of the present invention includes using visual guidance to navigate an interventional device 100, 500 of the present invention. In this embodiment, the user or medical personnel observes real-time or near real-time image data from the scanner or imaging apparatus, visually identifies the needle in the image and its location with respect to a target site. The user, physician, medical personnel using hand-eye coordination, continually actuates and repositions the interventional device till the end-effector and needle reaches the intended position or target site. In this way, the user, physician, or medical personnel manually navigates the interventional device so the needle 350 is deployed to the target site. Consequently, a plurality or more of placements or deployments of the needle 350 may be required before satisfactory needle placement is achieved.

While the actuation of the interventional device 100, 500 is in progress, the MRI scanner 1020 is collecting images in continuous mode and sends them immediately to the treatment monitoring computer 1010. The computer 1010 processes the image data and visualizes the current image, with the model of the interventional device superimposed in the scene, allowing the physician to monitor the motion of the interventional device and/or needle 350 thereof toward its target. The three parameters of motion (translation, rotation, insertion depth) are recalculated in each imaging cycle, enabling real-time dynamic control of the interventional device such as for example, by adjusting the actuation of motors or other actuation devices of the interventional device. It also is contemplated, and thus within the scope of the present invention, that when a surgeon points and clicks on a target in a computer screen, a robot controls the operation of the insertion stage 250 so as to move the needle 350 and inserts it into the target, under real-time imaging surveillance but without manual intervention.

In addition, to use of the interventional device 100, 500 of the present invention to take tissue biopsies, it also is contemplated that the scope of the methodologies and systems of the present invention includes delivery of therapeutic mediums, medical devices via the inserted needle and that such insertion can be performed one or more times and at different locations or target sites within a predetermined volume of tissues of the subject. In particular embodiments, it is contemplated that the placement of the needle 350 within the prostate or other tissues of the body (e.g., cervix or vagina) provides a mechanism by which a therapeutic medium (including but not limited to drugs, genes, viruses and photodynamic substances) or diagnostic agents (including but not limited to molecular imaging agents) can be delivered to a desired target site(s) using the inserted needle of the interventional device. It also is contemplated that the cannula or lumen formed by the inserted needle can be utilized to insert medical devices through the needle and so as to be localized to the target site(s) so as to perform one of brachytherapy, or tissue ablation (including thermal, cyro, ultrasonic, chemical ablation). Further, it also is contemplated that the interventional device and related systems and methods can be adapted for use with any of a number of medical imaging or scanning techniques including conventional X-ray, fluoroscopy, bi-planar fluoroscopy, CT X-ray, MRI, and ultrasonic imaging.

Figure 18:
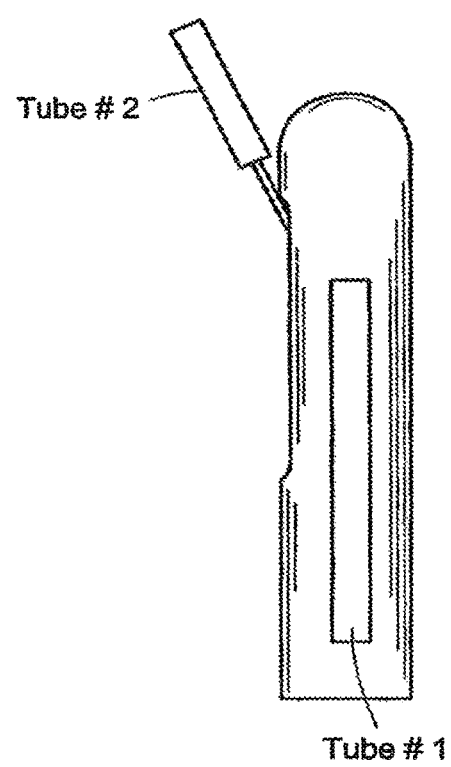
FIG. 18 is a schematic view of an end-effector with the needle in an inserted position for illustrating a calibration method of the present invention.

According to another aspect of the present invention, there is featured a calibration methodology to determine the signal center of each MRI registration coil with respect to the needle in the end-effector. This information is constant for the entire lifetime of the device, provided the same image acquisition and processing parameters are used during operation. As illustrated in FIG. 18, two tubes filled with gadolinium solvent producing a strong image signal are applied to the end-effector. In particular, a first tube is placed inside the end-effector in its central axis, while the second tube is attached to the needle 350 in a way that the central axes of the tube and the needle coincide. The end-effector/interventional device is carefully imaged in a MRI scanner and the central axes of the two tubes as well as the positions of fiducial coils are reconstructed from the high-resolution volumetric data. Using this information one determines the three dimensional relationship between the trajectory of the needle and the three registration coils of the end-effector.

As indicated above, the interventional devices and related systems, and apparatuses of the present invention are configured and arranged so as to administer/deliver a therapeutic medium to the target tissues of a target site. The therapeutic medium can comprise a therapeutic agent or a therapeutic agent in combination with a contrast agent to facilitate the imaging (e.g., MR imaging) of the therapeutic agent. In the present invention, therapeutic agent shall be understood to encompass or include, but are not limited to drugs, genes, nucleic acid molecules including encoding different types of nucleic acid molecules, an angiogenic factor, a growth factor, a chemotherapeutic agent, a radionuclide, a protein, a polypetide, a peptide, a viral protein, a lipid, an amphiphile, a nuclease inhibitor, a polymer, a toxin, a cell, and modified forms and combinations thereof that are used in therapeutic procedures in connection with the injury, insult, trauma or ischemia to the tissues or cells of the target site that is accessed via a lumen or body cavity of the mammalian body, more particularly a human body, more specifically, the vascular system of a human body. In addition, the therapeutic agent can be in an encapsulated form for long term sustained delivery to the target tissues.

The nucleic acid molecule is preferably provided in a nucleic acid delivery vehicle which is lipid-based, viral-based, or cell-based. More preferably, the vector comprises a gene operably linked to an expression control sequence. In one aspect, the nucleic acid molecule comprises a sequence encoding a polypeptide for preventing, correcting and/or normalizing an abnormal physiological response, such as a disease. Exemplary polypeptides include, but are not limited to, hirudin, tissue plasminogen activator, an anchored urokinase activator, a tissue inhibitor of metalloproteinase, proliferating cell nuclear antigen, an angiogenic factor, a tumor suppressor, a suicide gene and a neurotransmitter. The vector may comprise sequences to facilitate its delivery to, or expression in, a target cell. For example, the vector may comprise a marker gene (e.g., encoding a fluorescent protein) and/or an origin of replication for a host cell and/or target cell.

In the case where the therapeutic medium is being delivered and the particular imaging technique is being performed to track and observe the efficacy of such delivery, the therapeutic medium is a therapeutic composition that includes a therapeutic agent as hereinabove described and a contrast agent appropriate for the particular imaging technique being utilized. In a particular embodiment, the imaging technique is any of a number of MR/NMR imaging techniques and thus the contrast agent a magnetic resonance imaging contrast agent.

MRI contrast agents primarily act by affecting T1 or T2 relaxation of water protons. Most MRI contrast agents generally shorten T1 and/or T2. When contrast agents shorten T1, this increases signal intensity on T1 weighted images. When contrast agents shorten T2, this decreases signal intensity particularly on T2 weighted pulse sequences. Thus, preferably, contrast agents used in the invention have adequate nuclear or relaxation properties for imaging that are different from the corresponding properties of the cells/tissue being imaged. Suitable contrast agents include an imageable nucleus (such as $^{19}F$), radionuclides, diamagnetic, paramagnetic, ferromagnetic, superparamagnetic substances, and the like. In a preferred aspect, iron-based or gadolinium-based contrast agents are used, where Iron-based agents include iron oxides, ferric iron, ferric ammonium citrate and the like. Gadolinium based contrast agents include diethylenetriaminepentaacetic (gadolinium-DTPA). Manganese paramagnetic substances also can be used. Typical commercial MRI contrast agents include Omniscan, Magnevist (Nycomed Salutar, Inc.), and Pro-Hance.

In one preferred embodiment, gadolinium is used as the MRI contrast agent. Less than about 28.14 mg/mL gadolinium (such as less than 6% Magnevist) is an adequate concentration for imaging and is minimally destructive of nucleic acid delivery vehicles. However, it is well within the skill of those in the art to vary and optimize the amount of contrast agent to add to the compositions depending on the nature of the contrast agent (e.g., their osmotic effects) and the length of time during which a target cell is exposed.

In other embodiments, the composition comprises a pharmaceutically acceptable carrier. Preferably, the carrier is non-toxic, isotonic, hypotonic or weakly hypertonic and has a relatively low ionic strength (e.g., such as a sucrose solution). Furthermore, it may contain any relevant solvents, aqueous or partly aqueous liquid carriers comprising sterile, pyrogen-free water, dispersion media, coatings, and equivalents, or diluents (e.g. Tris-HCI, acetate, phosphate), emulsifiers, solubilizers and/or adjuvants. The pH of the pharmaceutical preparation is suitably adjusted and buffered in order to be appropriate for use in humans or animals. Representative examples of carriers or diluents for an injectable—composition include water or isotonic saline solutions which are preferably buffered at a physiological pH (e.g., such as phosphate buffered saline, Tris buffered saline, mannitol, dextrose, glycerol containing or not polypeptides or proteins such as human serum albumin). The compositions also can comprise one or more accessory molecules for facilitating the introduction of a nucleic acid delivery vector into a cell and/or for enhancing a particular therapeutic effect.

The foregoing is illustrative and shall not be considered limiting as the drugs or therapeutic compounds or agents, carriers, and accessory molecules that can be used to comprise the therapeutic medium of the present invention. Applicants also herein incorporate by reference the teachings and disclosures in their entirety of pending U.S. application U.S. Ser. No. 10/116, 708 entitled Imaging Nucleic Acid Delivery and in particular those teachings and disclosures of the various therapeutic agents described therein, which invention is assigned to the assignee of the present invention,

EXAMPLE

A mechanically actuated, transrectal needle guide is used to perform MR guided needle placements in the prostate.

With a microcoil tracking method, the position and orientation of the biopsy needle guide in the MR imaging volume (60 msec) could be quickly and accurately located. Knowing the position of the biopsy needle allows for acquisition of realtime images of a plane including the needle and registration of the needle position with previously acquired, high-resolution images of the prostate. In four canine studies, the functionality and applications of a system was demonstrated.

A thin-walled, cylindrical plastic sheath (Delrin plastic, DuPont Inc., Wilmington, Del.) with a radius of 1.5 cm is inserted into the subject's rectum, forming a stable and stationary entry point through which the prostate can be accessed. Integral to the sheath is a single turn imaging loop (with a diameter of 2.5 cm) for local imaging of the prostate. The sheath has a window, located within the imaging loop, such that a needle can be advanced from inside the sheath, through the rectal wall, and into the body of the prostate.

Next, a cylindrical needle guide, also made of Delrin plastic, is placed within the rectal sheath. As the needle guide is coaxial with the rectal sheath, the needle guide is free to rotate and translate within the cavity formed by the sheath without causing deformation of the surrounding soft tissue. Integral to the needle guide are (1) three microcoil fiducials and (2) a curved channel for the needle. Note that because the needle channel is curved, the needle can be inserted along the axis of the needle guide and emerge out of its lateral wall, allowing for access to the prostate through the window in the stationary rectal sheath.

Next, both the rectal sheath and the needle guide are affixed to a positioning stage made of Nylon plastic (QTC, New Hyde Park, N.Y.) and Delrin. First, the positioning stage serves to hold the rectal sheath stationary within the subject's rectum. A linear track (aluminum rail, 80/20 Inc., Columbia City, Ind.) and a polyamide plastic articulated-arm with six joints that are operably connected to the positioning stage allow for full mobility of the positioning stage, such that it can be easily docked with the rectal sheath, at which point the linear track and articulated arm are locked down to prevent any subsequent motion.

In addition to holding the rectal sheath stationary, the positioning stage contains a screw drive mechanism that allows for both rotation and translation of the needle guide. This device converts rotation of two concentric control rods (Epoxy tubing, TAP Plastics, Dublin, Calif.), both of which extend outside of the scanner bore, into rotation and translation of the needle guide. This allowed the operator to position the needle guide while the subject is within the closed bore scanner.

As the entire device is constructed with a coaxial design, the central axis offers an unobstructed path for insertion of the needle. The depth of needle insertion is controlled using a variable offset stop that is inserted at the back of the device before introducing the needle. An 18G coaxial biopsy needle (MRI Devices Daum GmbH, Schwerin, Germany) is inserted such that the needle tip emerges from the side of the needle guide.

Device Tracking, Prostate Targeting, and Realtime Imaging

MR pulse sequences and hardware were designed to facilitate targeted needle placement in the prostate within a GE 1.5 T CV/i MRI scanner with 4 independent receiver channels. Three microcoil fiducials were integrated within a transrectal needle guide, each connected to a separate receiver channel. To determine the position and orientation of these coils, twelve 1-D dodecahedrally spaced readouts were collected (TE 2.3 msec, TR 5.0 msec, BW +/−64 KHz, FA 1°, FOV 40 cm, 256 readout points), allowing for coil localization [Dumoulin C L, Souza S F, Darrow R D. Real-time position monitoring of invasive devices using magnetic resonance. Magn Reson Med 1993; 29:411-415; Derbyshire J A, Wright G A, Henkelman R M, Hinks R S. Dynamic scan-plane tracking using MR position monitoring. J Magn Reson Imaging 1998; 8:924-932]. The coil localization scan occupied ~60 msec. Microcoil location errors due to gradient nonlinearity were removed using gradient dewarping algorithms (GE Medical Systems, Waukesha, Wis.).

Given the position of the three microcoil fiducials in the MR coordinate system and the location of a given intraprostatic target (also in the MR coordinate system), the remaining problem is to determine (1) the rotation and translation necessary to position the needle guide such that the needle trajectory is aligned with the target and (2) the amount of needle insertion necessary to reach the target. This can be calculated using a set of coordinate transformations—assuming that the relationship between the microcoil positions, the device axis, and the needle trajectory are all known. These relationships are established using a device calibration scan in which Gd-DTPA (Magnevist, Berlex Laboratories, Wayne, N.J.) fiducial tubes define the device axis and the needle trajectory (the same, single calibration scan was used for all studies described here). In addition to determining the rotation and translation necessary to reach the target site, the calibration of the microcoil positions with the needle trajectory allowed for definition of a scan plane that includes both the needle path and the device axis. 'Realtime' images were acquired based on the current position of the microcoil fiducials, such that the needle could be visualized as it was inserted into the prostate.

All experiments were performed on a GE 1.5 T CV/I MRI scanner (GE Medical Systems, Waukesha, Wis.). A fast gradient-echo pulse sequence (FGRE) was modified to allow for alternating acquisition of the microcoil-tracking readouts (i.e. the twelve, dodecahedrally spaced readouts) and realtime FGRE images. After the location of each coil was determined, the position and orientation of the imaging plane is defined such that the realtime FORE image slice tracked with the position of the needle.

Realtime data processing and display were performed using a Sun Ultra II Workstation (Sun Microsystems, Mountain View, Calif.) connected to the scanner with a high-bandwidth data bus (Bit3 Corporation, St Paul, Minn.). In the current implementation, the tracking sequence takes 60 msec; image processing, communication, and scan plane localization occupies 150 msec; and imaging takes 300 to 1300 msec—yielding frame rates of 0.7 to 2 fps (depending predominantly on image acquisition time). Images were acquired using a rectal imaging coil while the other three receiver channels were used for the microcoil fiducials.

Animal Protocol

All animal protocols were reviewed and approved by the Animal Care and Use Committee at the Johns Hopkins University School of Medicine. Four mongrel dogs weighing approximately 25 kg were anesthetized with a bolus injection of thiopental and maintained on 1% isoflurane throughout the experiment. An intravenous catheter was placed in the right jugular vein for fluid administration and a Foley catheter was inserted to aid in stabilizing the prostate and to define the position of the prostatic urethra. The animals were placed prone on the scanner table with the pelvis slightly elevated (~10 cm) with a 5-inch surface coil on the anterior surface of the abdomen at the level of the prostate. The rectal sheath was inserted into the rectum and docked with the positioning apparatus, which was then locked in place.

Needle Placement Protocol

In the first animal study, the accuracy of needle placement was tested in-vivo. After the animal was positioned in the scanner, T1 weighted FSE images of the prostate and surrounding anatomy were acquired (TE 9.2 msec, TR 700 msec, BW +/−31.25 KHz, ETL 4, FOV 16 cm, slice thickness 3 mm, 256×256, NEX=4, scan time 3:00). Two receiver channels were used for these images: one for the 5-inch surface coil and one for the rectal coil. In these images, a target was selected within the body of the prostate and entered into the realtime control program. Scanning was then switched to the realtime FGRE imaging and tracking sequence.

While running the realtime FGRE imaging and tracking sequence, the operator is able to rotate and translate the needle guide from the mouth of the scanner bore using the control rods. On a scan room flat panel display, the operator watches both the realtime image slice, showing the trajectory of the needle, as well numerical values indicating the current amount of rotation and translation necessary to set the correct needle trajectory. As the needle guide is moved closer to the target position, these numbers move to zero— indicating that no more rotation or translation is necessary.

Once the needle guide on the proper trajectory, the insertion stop is set to the proper depth (also indicated on the flat panel display) and the needle is pushed until it is flush with the stop. The insertion of the needle can be visualized on the scan room display and once in place, the needle tip will be at the desired target location.

To confirm the location of the needle tip, a second set of T1 weighted FSE images were acquired. This protocol was repeated for four separate needle insertions.

Intraprostatic Injection Protocol

To demonstrate MR monitored injection therapies, intraprostatic injections were preformed in two canine subjects. Similar to the needle placement protocol, targets in the prostate were selected on axial T1 weighted FSE images and the needle tip was placed at these locations using the realtime FORE imaging and tracking sequence. After the coaxial needle was placed, the trocar (i.e. an inner stylus) was withdrawn, leaving only the 18G cannula (i.e., a hollow metal tube) in place. This provided a conduit through which injections into the body of the prostate could be performed.

In this demonstration, a mixture of 0.4% Trypan Blue (Sigma-Aldrich, St. Louis, Mo.) and 30 mM Gd-DTPA (Magnevist, Berlex Laboratories, Wayne, N.J.) was injected, in particular 0.3 mL of this solution was injected into the prostate. During the injection, the flow of the mixture was monitored using a high flip-angle, RF-spoiled, gradient echo imaging sequence (FSPGR, TE 1.5 msec, TR 6 msec, FA 90°, BW +/−62.5 KHz, FOV 16 cm, slice thickness 10 mm, 256×160, 0.96 sec/image). The location of the injected solution was determined by comparing gradient echo axial images acquired both before and after the injection (FSPGR, TE 2.0 msec, TR 80 msec, FA 60°, BW +/−31.25 KHz, FOV 16 cm, slice thickness 3 mm, 256×256, NEX 4, scan time 1:20).

Brachytherapy Seed Placement Protocol

In a fourth canine, the use of the device for MR guided brachytherapy seed placement was demonstrated. Targets were selected and the trocar and canula were placed, as described previously. Then, to insert the titanium brachytherapy seeds (OncoSeed blanks, Medi-Physics Inc., Arlington Heights, Ill.), the trocar was withdrawn, leaving the hollow cannula in place within the prostate, A brachytherapy seed was inserted into the cannula and then advanced to the end, but not out, of the cannula by pushing it with another trocar. With the seed at the end of the cannula, the cannula was withdrawn slightly while holding the trocar stationary, causing the brachytherapy seed to be ejected into the prostate tissue. Subsequently, the trocar and cannula were both withdrawn together.

Three seeds were placed using this technique. The location of the needle and of the seeds was confirmed using T1 weighted FSE images (TE 9.2 msec, TR 700 msec, BW +/−31.25 KHz, ETL 4, FOV 16 cm, slice thickness 3 mm, 256×256, NEX=4, scan time 3:00).

Results

Figure 19:
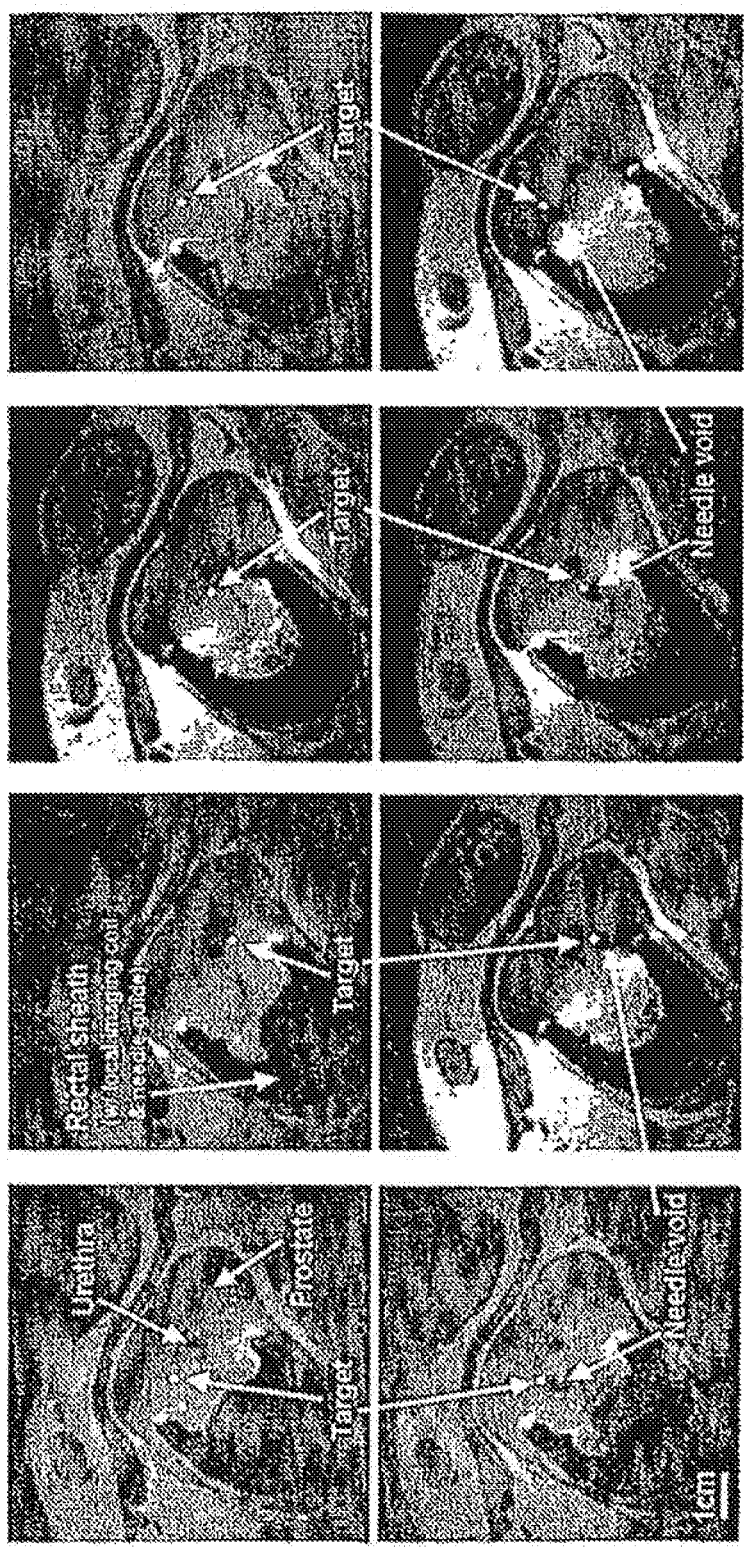
FIG. 19 In an anesthetized canine, four targets were selected from T1 weighted FSE images (top row) (TE 9.2 msec, TR 700 msec, BW +/−31.25 KHz, ETL 4, FOV 16 cm, slice thickness 3 mm, 256×256, NEX=4, scan time 3:00). FSE images were repeated after needle placement (bottom row).

In the first canine subject, accurate needle placement within the body of the prostate is demonstrated. The results of this study are summarized in FIG. 19. In sequential order, four targets were selected from T1 weighted FSE images (FIG. 19, top row). Having placed the needle using the FORE realtime imaging and tracking sequence, FSE images were repeated to confirm placement of the needle by visualizing the needle void (FIG. 19, bottom row). In all cases, the end of the needle artifact was found in the same image slice as the target. Moreover, the center of the needle tip void was found within 2 mm of the selected target. Note also that there is minimal motion of the prostate upon insertion of the needle.

Figure 20:
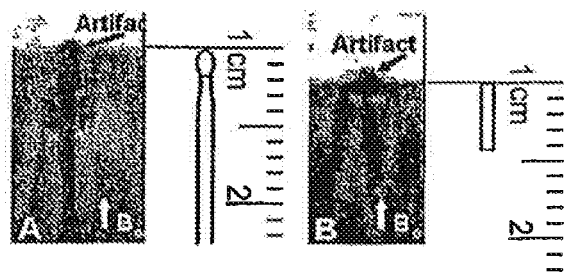
FIG. 20 Artifacts created by prostate needle (Panel a) and brachytherapy seed (Panel b) (FSE, TE 9.2 msec, TR 700 msec, BW +/−31.25 KHz, ETL 4, FOV 8 cm, slice thickness 1.5 mm, 256×256, NEX=4, scan time 3:00). Both objects create a uniform signal void along their length and a circular bloom, centered on the object tip, at the end facing the positive pole of the main field. Artifacts were aligned by placing the physical objects at the interface of gadolinium doped and gadolinium free gel blocks.

For interpretation of these results, it is useful to examine the artifact created by the 18G MR compatible needle. FIG. 20 shows the artifact created both by the needle and by a brachytherapy seed. Artifacts were aligned by placing the physical objects at the interface of gadolinium doped and gadolinium free gel blocks. Note that the tip void is a circular bloom that is centered on the physical end of the needle, as has been previously reported when the needle is aligned approximately parallel to $B_0$ with the tip toward the positive magnet pole [Liu H, Martin A J, Truwit C L. Interventional MRI at high-field (1.5 T): needle artifacts. J Magn Reson Imaging 1998; 8:214-219]. In all cases, because of the design of the needle placement system, the needle is approximately parallel to $B_0$ and therefore, the artifact provides a good estimate of the needle tip position.

Figure 21:
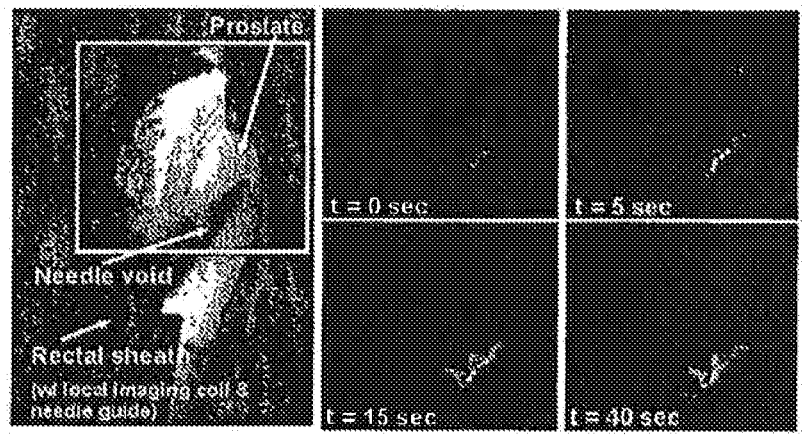
FIG. 21 Intraprostatic injections (here, a solution of 0.4% Trypan Blue and 30 mM Gd-DTPA) can be visualized under MRI. The white box on the sagittal scout (left image) shows the location of the time series images. Note that all of the injected contrast/dye solution stays confined within the prostate. Therefore, it was confirmed that the full, desired dose was delivered to the tissue. (FSPGR, TE 1.5 msec, TR 6 msec, FA 90°, BW +/−62.5 KHz, FOV 16 cm, slice thickness 10 mm, 256×160, 0.96 sec/image).

In two canine subjects, the use of the system for MR monitored intraprostatic injections was demonstrated. First, a target within the body of the prostate gland was selected and the needle was positioned as described in the previous section. Then, the trocar was withdrawn, leaving the cannula as a conduit into the prostate. A mixture of 30 mM Gd-DTPA and 0.4% Trypan Blue [Yang X, Atalar E, Li D, et al. Magnetic resonance imaging permits in vivo monitoring of catheter-based vascular gene delivery. Circulation 2001; 104:1588-1590] was then injected into the prostate. A high flip-angle, RF-spoiled, gradient echo acquisition was run during the injection of 0.3 mL of this solution. The box on the sagittal scout (FIG. 21, left image) shows the location of the time series images. Note that all of the injected contrast/dye solution stays confined within the prostate. Therefore, it was confirmed—during the injection—that the full, desired dose was delivered to the prostate tissue.

Figure 22:
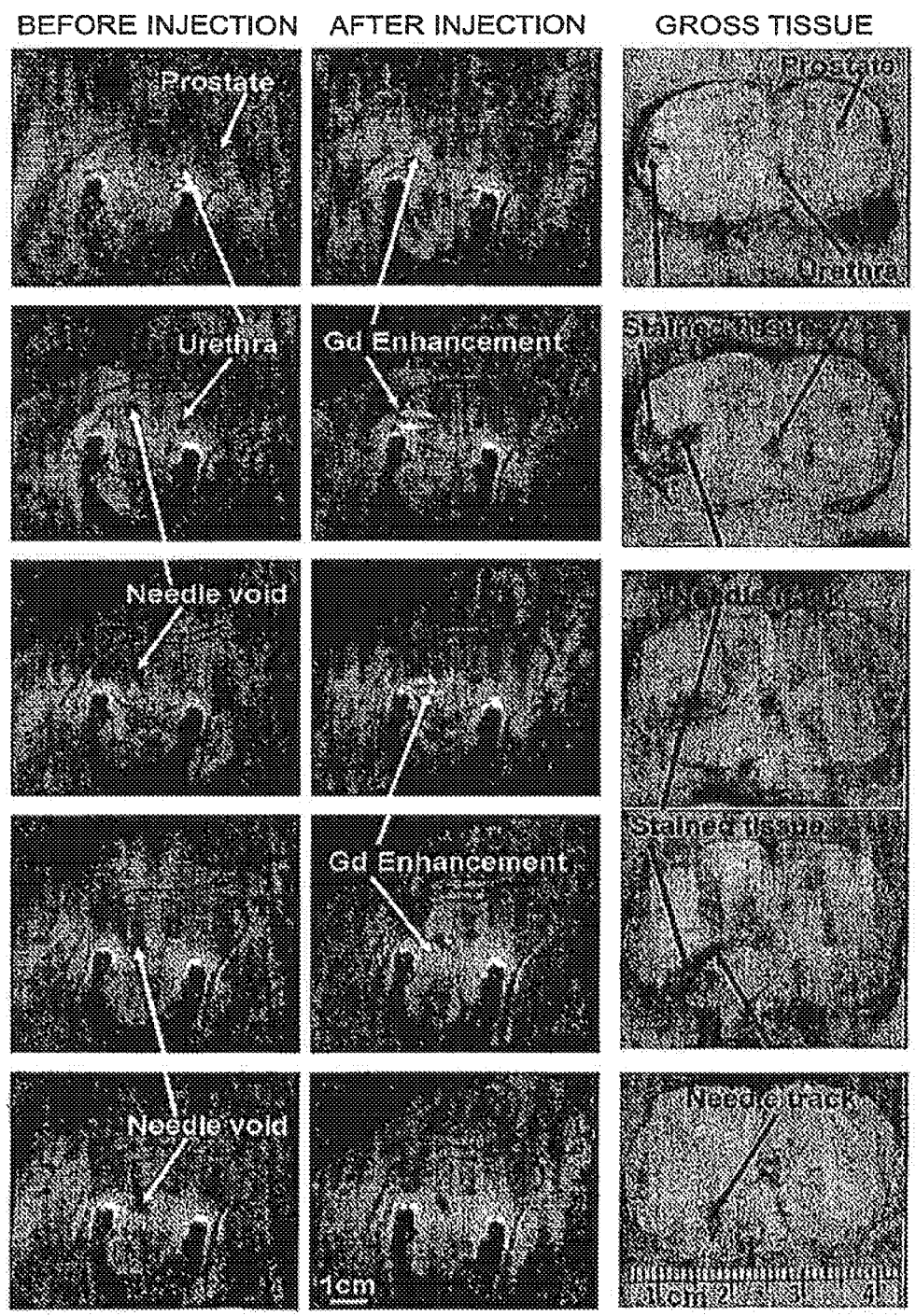
FIG. 22 The distribution of injected material visualized in MR images reflects the actual, histologically confirmed distribution. Gadolinium-DTPA location (enhancement seen in post—but not pre-injection images) matches with blue stained tissue in the canine prostate (FSPGR, TE 2.0 msec, TR 80 msec, FA 60°, BW +/−31.25 KHz, FOV 16 cm, slice thickness 3 mm, 256×256, NEX 4, scan time 1:20).

In FIG. 22, the distribution of the mixture as shown in the MR images is compared with that revealed on histology. There is good correlation between the tissue enhancement (seen in the second column, after the injection, but not in the first column, before the injection) and the tissue stained with the Trypan Blue dye (FIG. 22, third column).

Figure 23:
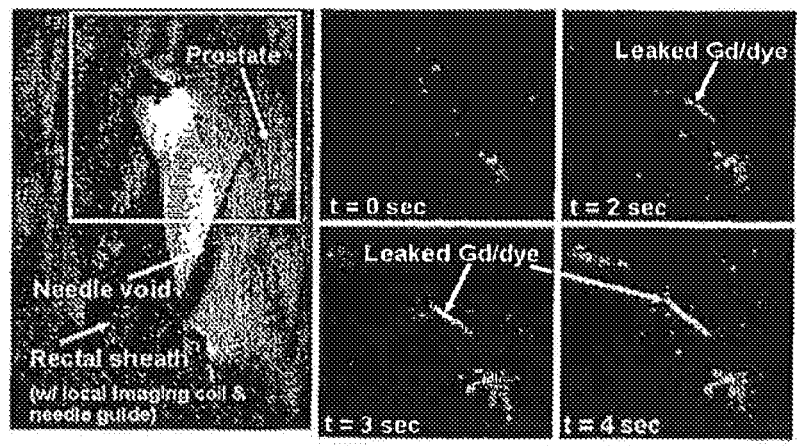
FIG. 23 MRI monitoring allows for detection of faulty injections. The white box on the sagittal scout (left image) shows the location of the time series images. In this canine, the injected contrast/dye solution leaked out of the prostate and into surrounding connective tissue. Therefore, it is known—during the procedure—that the desired dose has not been delivered to the prostate.
Figure 24:
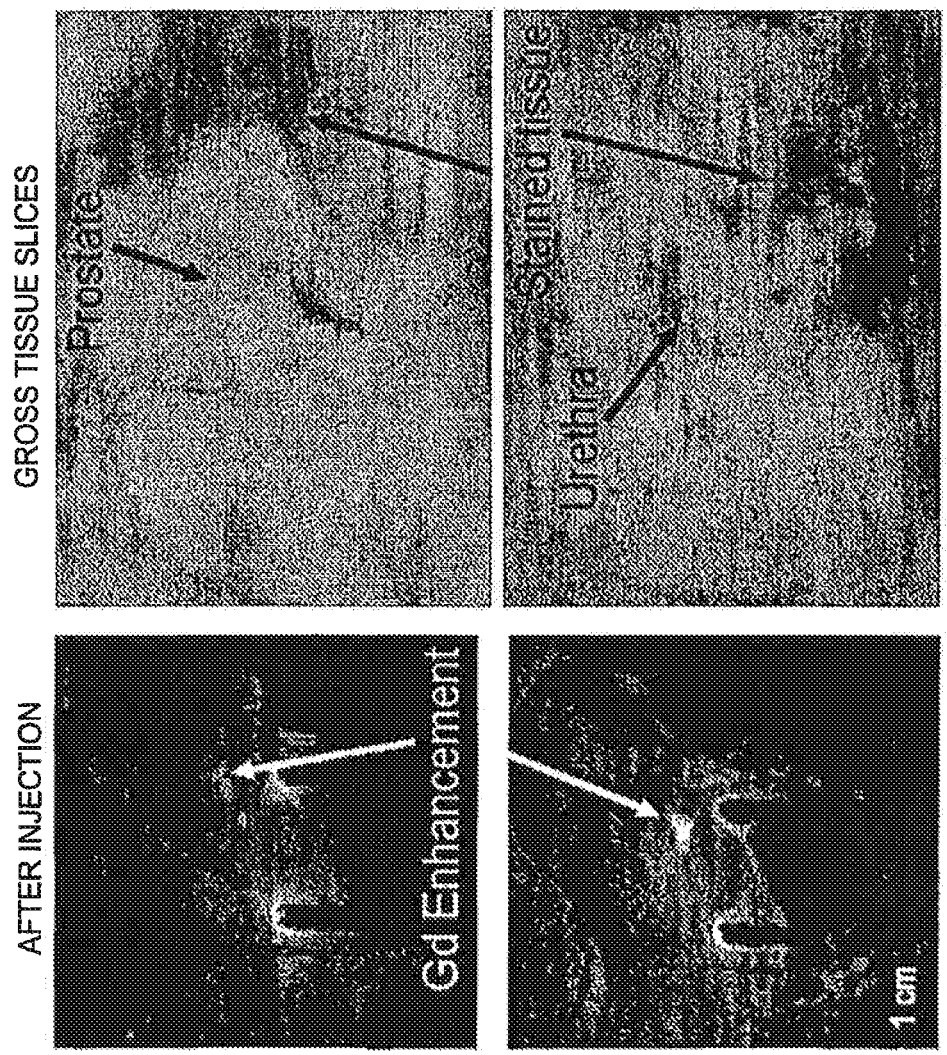
FIG. 24 In both MR images and histological sections, leakage of the injected solution into surrounding tissue is continued. Gadolinium-DTPA location (bright enhancement seen in MR images) correlates with blue stained tissue in canine prostate sections. While some contrast and dye remained within the prostate, additional solution passed into connective tissue at the superior, left, posterior prostate margin.

In the next canine, the injection protocol was repeated as before. In this case, however, the injected contrast/dye solution is seen to leak out of the prostate and into the surrounding connective tissue (FIG. 23). Therefore, it is known—during the procedure—that the desired dose has not been delivered to the prostate. In FIG. 24, the presence of Trypan Blue in connective tissue at the superior margin of the prostate is confirmed histologically.

Figure 25:
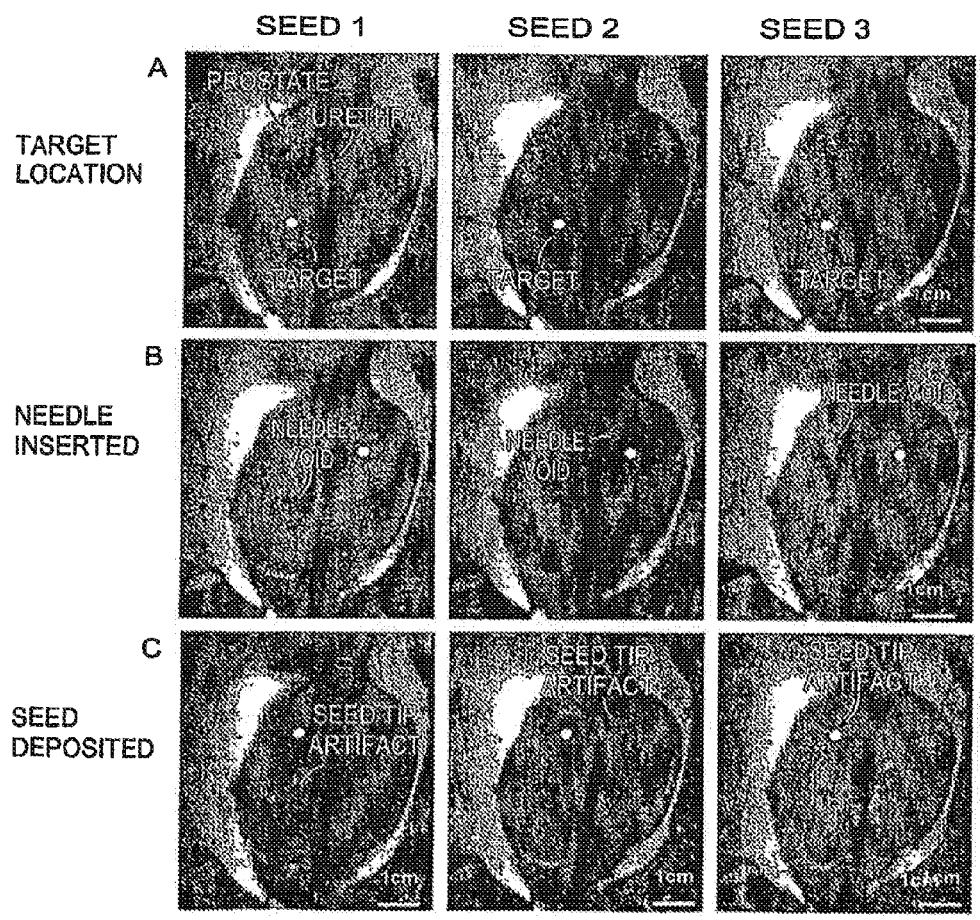
FIG. 25 MRI guidance allows for accurate placement of brachytherapy seeds within the prostate. Three targets were selected in a single coronal plane within the prostate (row a) (FSE, TE 9.2 msec, TR 700 msec, BW +/−31.25 KHz, ETL 4, FOV 16 cm, slice thickness 3 mm, 256×256, NEX=4, scan time 3:00). The needle was placed at these locations as described previously (row b). As the brachytherapy seeds are placed at the end of the canula (2 mm back from the end of the trocar tip), the needle artifact is seen to extend beyond the target site by approximately 2 mm. In row c, the seeds have been placed within the prostate. The black, bloom artifact at the superior end of the 4 mm brachytherapy seeds is visible. The seeds extend 4 mm in the inferior direction from this artifact.

In the last canine subject, the application of the system for placing brachytherapy seeds within the prostate is demonstrated. The results of this study—in which three seeds were placed in the prostate—are summarized in FIG. 25. As described previously, three targets were selected, in succession, within the body of the prostate (FIG. 25, row a) and the needle was placed using the realtime FGRE imaging and tracking sequence (FIG. 25, row b). As compared with the needle placement study (FIG. 19), the tip of the needle artifact is seen to extend beyond the target point. This is because the brachytherapy seeds are placed at the end of the cannula, not at the end of the trocar. The trocar extends 2 mm past the end of the cannula. Therefore, for proper seed deposition, the trocar must extend 2 mm past the target point, as seen in FIG. 25, row b.

In FIG. 25, row e, the seeds are placed in the prostate and the coaxial needle has been removed. To interpret these results, refer to FIG. 20, where the artifact pattern for the brachytherapy seeds is displayed. The main signal void is found at the end of the 4 mm seed that lies nearest to the positive pole of $B_0$. This corresponds to the black void seen in FIG. 25, row c. The body of the brachytherapy seeds extend 4 mm in the inferior direction from this void (in the direction of the target location). The seeds lie within 3 mm of the selected target location. Also, note that intraprostatic bleeding, resulting from seed placement, can be seen near seeds 2 and 3 (i.e. the dark banding radiating toward the edge of the prostate).

Although a preferred embodiment of the invention has been described using specific terms, such description is for illustrative purposes only, and it is to be understood that changes and variations may be made without departing from the spirit or scope of the following claims.

The invention claimed is:

1. An apparatus comprising:
   an end member, a portion of which is configured to be inserted into one of a natural cavity or an artificially formed cavity of a subject while the subject is within an imaging field of a medical imaging apparatus; and
   wherein said end member includes:
      a carrier member configured to be one of translatably or rotatably disposed inside a sheath member so that translation or rotation of the carrier member is not imparted to the sheath member,
         wherein the carrier member is configured to have a passage for a medical device that can be movably received and selectively deployed therefrom between a stored position and a deployed position,
         wherein the deployed position of the carrier member is configured so that a portion of the medical device penetrates target tissues located about said one of the natural or artificial body cavity into which said end member is inserted.

2. The apparatus of claim 1, wherein the sheath member is configured and arranged to be received with said one of natural or artificial body cavity.

3. The apparatus of claim 2, wherein the sheath member is configured so as to include a through aperture that communicates with the sheath member interior compartment and which extends partially circumferentially and partially longitudinally so as to form a window in an exterior surface of the sheath member, where the medical device passes through the window when being deployed.

4. The apparatus of claim 1, wherein said end member further includes an imaging device that is configured and arranged so as to allow a volume of tissues including the target tissues to be imaged.

5. The apparatus of claim 2, wherein said end member further includes an MRI receiver antenna, the MRI receiver antenna being configured and arranged so as to MR/NMR image a volume of tissues including the target tissues.

6. The apparatus of claim 5, wherein the sheath member is configured so as to include a through aperture that communicates with a sheath member interior compartment and which extends partially circumferentially and partially longitudinally so as to form a window in an exterior surface of the sheath member, wherein the MRI receiver antenna is arranged so as to image tissues opposite the sheath member through aperture, and wherein the medical device passes through the window when being deployed.

7. The apparatus of claim 6, wherein the MRI receiver antenna comprises an MRI coil antenna and wherein said sheath member is configured and arranged so that the MRI coil antenna is disposed about at least a portion of a perimeter of the sheath member through aperture.

8. The apparatus of claim 1, wherein said end member further includes an ultrasonic imaging device that is configured and arranged so as to image a volume of tissues including the target tissues.

9. The apparatus of claim 8, wherein the carrier member is configured and arranged so that the ultrasonic imaging device is disposed therein proximal a location from which the medical device is deployed therefrom.

10. The apparatus of claim 2, further comprising:
   a positioning mechanism operably coupled to the carrier member; and
   wherein said positioning mechanism is configured and arranged so as to cause the carrier member to one of translate or rotate within the sheath member interior compartment.

11. The apparatus of claim 10, wherein said positioning mechanism is configured and arranged so as to selectively rotate or translate the carrier member.

12. The apparatus of claim 1, wherein said end member further includes one or more tracking devices, each of said one or more tracking devices being configured and arranged so a position of each tracking device can be determined using an imaging system external to the apparatus.

13. The apparatus of claim 12, wherein the one or more tracking devices are passive fiducials appropriate for the particular imaging technique embodied in the external imaging system.

14. The apparatus of claim 12, wherein the one or more tracking devices are arranged so as to allow a determination to be made of an amount the carrier member is being translated or rotated r.

15. The apparatus of claim 12, wherein said end member further includes a plurality or more tracking devices.

16. The apparatus of claim 15, wherein the plurality or more of tracking devices are arranged so as to allow a determination to be made of an amount the carrier member is being translated or rotated.

17. The apparatus of claim 12, wherein the external imaging system is an MRI imaging system and wherein the one or more tracking devices comprise one of a passive fiducial or a tracking coil.

18. The apparatus of claim 17, wherein one of the passive fiducials or the tracking coils are arranged so as to allow a determination to be made of an amount the carrier member is being translated or rotated.

19. The apparatus of claim 18, wherein said end member comprises three tracking coils being arranged so as to allow a determination to be made of an amount the carrier member is being translated or rotated.

20. The apparatus of claim 19, wherein said end member includes passive fiducials.

21. The apparatus of claim 1, wherein the passage is configured and arranged so an exit thereof is from a surface of the carrier member.

22. The apparatus of claim 21, wherein a portion of the passage proximal the exit is arcuate.

23. The apparatus of claim 22, further comprising a mechanism operably coupled to the medical device, said mechanism being configured so as to rotate the medical device as the medical device traverses at least a portion of the passage.

24. The apparatus of claim 22, wherein the passage includes a flexible portion proximal the exit and wherein said carrier member further includes a mechanism operably coupled to the passage flexible portion, the mechanism being configured and arranged so as to selectively control one of a position of the exit with respect an exterior surface of the carrier member or an exit angle of the medical device with respect to the exterior surface of an axis of the carrier member.

25. The apparatus of claim 1, further comprising the carrier member configured to receive a mechanism for selectively controlling deployment of the medical device from the carrier member into the tissues.

26. The apparatus of claim 1, wherein the medical device is one of a needle or a flexible needle that is configured to penetrate tissues about the one of natural or artificial body cavity.

* * * * *

UNITED STATES PATENT AND TRADEMARK OFFICE
CERTIFICATE OF CORRECTION

PATENT NO. : 9,588,195 B2
APPLICATION NO. : 14/200910
DATED : March 7, 2017
INVENTOR(S) : Gabor Fichtinger et al.

It is certified that error appears in the above-identified patent and that said Letters Patent is hereby corrected as shown below:

In the Specification

Column 1 Line 19 replace with the following:
STATEMENT OF GOVERNMENTAL INTEREST
This invention was made with government support under grant number EEC9731478, awarded by the National Science Foundation. The government has certain rights in the invention.

Signed and Sealed this
Sixth Day of February, 2018

Joseph Matal
*Performing the Functions and Duties of the*
*Under Secretary of Commerce for Intellectual Property and*
*Director of the United States Patent and Trademark Office*